(12) United States Patent
Oh et al.

(10) Patent No.: US 10,456,112 B2
(45) Date of Patent: Oct. 29, 2019

(54) ULTRASOUND DIAGNOSIS APPARATUS, ULTRASOUND DIAGNOSIS METHOD AND COMPUTER-READABLE STORAGE MEDIUM

(71) Applicant: SAMSUNG MEDISON CO., LTD., Hongcheon-gun (KR)

(72) Inventors: Dong-hoon Oh, Hongcheon-gun (KR); Dong-gyu Hyun, Hongcheon-gun (KR)

(73) Assignee: SAMSUNG MEDISON CO., LTD., Hongcheon-gun (KR)

( * ) Notice: Subject to any disclaimer, the term of this patent is extended or adjusted under 35 U.S.C. 154(b) by 637 days.

(21) Appl. No.: 14/933,082

(22) Filed: Nov. 5, 2015

(65) Prior Publication Data
US 2016/0166238 A1 Jun. 16, 2016

(30) Foreign Application Priority Data
Dec. 15, 2014 (KR) ........................ 10-2014-0180493

(51) Int. Cl.
*A61B 8/00* (2006.01)
*A61B 8/08* (2006.01)
(Continued)

(52) U.S. Cl.
CPC ............... *A61B 8/467* (2013.01); *A61B 1/00* (2013.01); *A61B 8/085* (2013.01); *A61B 8/0891* (2013.01);
(Continued)

(58) Field of Classification Search
CPC ....... A61B 8/5207; A61B 34/10; A61B 8/463; A61B 8/483; A61B 8/467; A61B 8/0891; A61B 8/465; A61B 8/466; A61B 8/085; A61B 8/13; A61B 8/5223; A61B 8/523; A61B 8/5246; A61B 8/488; A61B 1/00;
(Continued)

(56) References Cited

U.S. PATENT DOCUMENTS 6,369,812 B1 * 4/2002 Iyriboz .................. A61B 6/463
345/419
2001/0031920 A1 * 10/2001 Kaufman ............... A61B 5/055
600/431
(Continued)

FOREIGN PATENT DOCUMENTS

| JP | 2014-003991 A | 1/2014 |
| KR | 10-1198608 B1 | 11/2012 |
| WO | 2014024995 A1 | 2/2014 |

OTHER PUBLICATIONS

Communication dated Apr. 19, 2016 issued by the European Patent Office in counterpart European Patent Application No. 15198247.7.
(Continued)

*Primary Examiner* — Bo Joseph Peng
(74) *Attorney, Agent, or Firm* — Sughrue Mion, PLLC

(57) ABSTRACT

An ultrasound diagnosis apparatus providing a user interface enabling a user to easily move viewpoint. The ultrasound diagnosis apparatus includes an image generating unit, which obtains a first ultrasound image by scanning a target object; and a control unit, which obtains first information including a plurality of nodes included in the first ultrasound image, moves a viewpoint based on the first information, and obtains second ultrasound images.

18 Claims, 17 Drawing Sheets

(51) Int. Cl.
  A61B 1/00    (2006.01)
  A61B 8/13    (2006.01)
  G06T 19/00   (2011.01)
  A61B 90/00   (2016.01)

(52) U.S. Cl.
  CPC .............. *A61B 8/13* (2013.01); *A61B 8/463* (2013.01); *A61B 8/465* (2013.01); *A61B 8/466* (2013.01); *A61B 8/483* (2013.01); *A61B 8/523* (2013.01); *A61B 8/5207* (2013.01); *A61B 8/5223* (2013.01); *A61B 8/5246* (2013.01); *G06T 19/003* (2013.01); *A61B 8/488* (2013.01); *A61B 2090/365* (2016.02); *G06T 2210/41* (2013.01)

(58) Field of Classification Search
  CPC ............ A61B 2090/365; G06T 19/003; G06T 2210/41
  See application file for complete search history.

(56) References Cited

U.S. PATENT DOCUMENTS

| | | |
|---|---|---|
| 2005/0245803 A1 | 11/2005 | Glenn, Jr. et al. |
| 2011/0184710 A1 | 7/2011 | Kwon et al. |
| 2013/0211243 A1 | 8/2013 | Zhang et al. |
| 2014/0094693 A1 | 4/2014 | Cohen et al. |
| 2014/0343408 A1 | 11/2014 | Tolkowsky |
| 2015/0150537 A1 | 6/2015 | Maruyama |

OTHER PUBLICATIONS

Norio Nakata, et al; "Ultrasound Virtual Endoscopic Imaging"; Seminars in Ultrasound; vol. 22; No. 1; XP055263201; Feb. 1, 2001; pp. 78-84.

Ming Wan, et al; "Automatic Centerline Extraction for Virtual Colonoscopy"; IEEE Transactions on Medical Imaging; vol. 21; No. 12; XP055263215; Dec. 1, 2002; pp. 1450-1460.

* cited by examiner

ULTRASOUND DIAGNOSIS APPARATUS, ULTRASOUND DIAGNOSIS METHOD AND COMPUTER-READABLE STORAGE MEDIUM

RELATED APPLICATION

This application claims the benefit of Korean Patent Application No. 10-2014-0180493, filed on Dec. 15, 2014, in the Korean Intellectual Property Office, the disclosure of which is incorporated herein in its entirety by reference.

BACKGROUND

1. Field

One or more exemplary embodiments relate to an ultrasound diagnosis apparatus, an ultrasound diagnosis method and a computer-readable storage medium, and more particularly, to an ultrasound diagnosis apparatus and an ultrasound diagnosis method for observing a plurality of regions during an ultrasound diagnosis and a computer readable recording medium having recorded thereon a computer program for implementing the method.

2. Description of the Related Art

An ultrasound diagnosis apparatus irradiates ultrasound signals generated by transducers of a probe to an object and receives ultrasound echo signals reflected from the object, thereby obtaining images regarding the interior of the object (e.g., tomography of soft tissues or blood flow). In particular, an ultrasound diagnosis apparatus may be used for medical purposes including observation of the interior of an object, detection of foreign substances, and diagnosis of damage. The ultrasound diagnosis apparatus may display information regarding an object in real time. Furthermore, unlike the use of X-rays, the ultrasound diagnosis apparatus does not involve any radioactive exposure, and thus is very safe to use. Therefore, the ultrasound diagnosis apparatus is widely used together with other types of imaging diagnosis apparatuses such as computer tomography (CT) scanners, magnetic resonance imaging (MRI) apparatuses, and nuclear medical diagnosis apparatuses.

Here, when a user, such as a doctor, moves a viewpoint of an ultrasound image using an input device, such as a trackball image, it is not easy to move the viewpoint of the ultrasound image if the user is not familiar with the input device. Furthermore, when a viewpoint of an ultrasound image is moved using a trackball, it is difficult for a user to recognize a path in which the viewpoint is moved. Therefore, it is necessary to provide a ultrasound diagnosis apparatus that enables a user to easily move a viewpoint of an ultrasound image.

When a user performs a ultrasound diagnosis with respect to a tubular target object, such as a blood vessel and a digestive system, it may be necessary to move a viewpoint to each of a plurality of terminal ends of the target object in turn. In a current ultrasound diagnosis apparatus, a viewpoint is moved by using a trackball. However, it is inconvenient for a user to move a viewpoint using a trackball one after another. Furthermore, a user is unable to recognize a path in which a viewpoint is moved after the viewpoint is moved.

SUMMARY

One or more exemplary embodiments include an ultrasound diagnosis apparatus and an ultrasound diagnosis method for easily moving viewpoints and a computer readable recording medium having recorded thereon a computer program for implementing the method.

Additional aspects will be set forth in part in the description which follows and, in part, will be apparent from the description, or may be learned by practice of the presented embodiments.

According to one or more exemplary embodiments, an ultrasound diagnosis apparatus includes an image generating unit, which obtains a first ultrasound image based on ultrasound data obtained by scanning a target object; and a control unit, which obtains first information including a plurality of nodes based on the ultrasound data, moves a viewpoint based on the first information, and obtains second ultrasound images.

The control unit obtains second information including at least one of location and direction of the viewpoint based on the first information, and the ultrasound diagnosis apparatus further includes a display unit, which displays an image in which at least one of the first information and the second information is displayed on the first ultrasound image.

The control unit obtains trunk lines interconnecting the nodes and the other nodes, the control unit obtains a structure included in the first ultrasound image based on the plurality of nodes and trunk lines, and the first information includes at least one of the trunk lines and the structure.

The control unit automatically obtains a sequence of nodes regarding at least two of the nodes, controls the image generating unit to move a viewpoint according to the obtained sequence of nodes, and to obtain the second ultrasound images.

The ultrasound diagnosis apparatus further includes an input unit, which receives an input related to first information from a user via a particular location of the first ultrasound image.

The control unit performs at least one of operations for adding, moving, and deleting at least one of the nodes and the trunk lines based on the received input.

The input unit receives an input for selecting at least one node from among the nodes from a user, and the control unit automatically obtains second ultrasound images based on the selected node(s).

The input unit receives an input for selecting at least one node from among the nodes from a user, and the control unit controls to automatically obtain second ultrasound images based on nodes other than the selected node(s).

The input unit receives an input related to a sequence of nodes regarding at least two from among the nodes from a user, and the control unit controls to move a viewpoint based on the received input related to the sequence of nodes and obtains second ultrasound images.

The input unit receives an input related to a speed of moving a viewpoint between nodes from a user, and the control unit controls to move the viewpoint based on the speed of moving a viewpoint and obtains the second ultrasound images.

The input related to a speed of moving a viewpoint includes moving time between nodes.

The control unit extracts first information including the nodes and the trunk lines from the ultrasound image by performing an image processing including a centerline extracting algorithm.

The control unit controls to move a viewpoint based on the first information and automatically obtains the second ultrasound images.

The control unit controls to move a viewpoint along trunk lines between the nodes and obtains second ultrasound images.

The control unit controls to display at least one of the nodes and the trunk lines passed by a viewpoint.

The control unit controls to display at least one from among the nodes and the trunk lines passed by a viewpoint in a transparency, a color, or a shape different from the nodes and the trunk lines not passed by the viewpoint.

The second ultrasound image includes a virtual endoscopic image based on ultrasound data.

The second ultrasound images include at least one of 2D images and 3D images.

The structure is a graph having a tree structure.

According to one or more exemplary embodiments, an ultrasound diagnosis apparatus includes an ultrasound data obtaining unit, which obtains ultrasound data obtained by scanning a target object; an input unit, which receives an input from a user; and a control unit, which obtains first information including a plurality of nodes based on the ultrasound data and controls to obtains ultrasound images by moving a viewpoint based on the first information and the received input.

According to one or more exemplary embodiments, an ultrasound diagnosis apparatus includes an ultrasound data obtaining unit, which obtains ultrasound data obtained by scanning a target object; a control unit, which obtains first information including at least one selected from a plurality of nodes and a plurality of trunk lines based on the ultrasound data and controls to move a viewpoint based on the first information; and a display unit, which displays first information passed by the viewpoint to be distinguishable from first information not passed by the viewpoint.

According to one or more exemplary embodiments, an ultrasound diagnosis apparatus includes an image generating unit, which obtains a first ultrasound image by scanning a target object; an input unit, which receives an input from a user; and a control unit, which obtains first information including a plurality of nodes included in the first ultrasound image based on the received input, obtains a sequence of nodes based on the received input, controls to move a viewpoint based on the sequence of nodes and the first information, and obtains second ultrasound images.

According to one or more exemplary embodiments, an ultrasound diagnosis method includes obtaining a first ultrasound image based on ultrasound data obtained by scanning a target object; obtaining first information including a plurality of nodes based on the ultrasound data; and moving a viewpoint based on the first information and obtaining second ultrasound images.

The ultrasound diagnosis method further includes obtaining second information including at least one of location and direction of the viewpoint based on the first information; and displaying an image in which at least one of the first information and the second information is displayed on the first ultrasound image.

The ultrasound diagnosis method further includes obtaining trunk lines interconnecting the nodes and the other nodes; and, based on the plurality of nodes and trunk lines, obtaining a structure included in the first ultrasound image, wherein the first information includes at least one of the trunk lines and the structure.

The obtaining of the second ultrasound images includes automatically obtaining a sequence of nodes regarding at least two of the nodes; and moving a viewpoint according to the obtained sequence of nodes, and to obtain the second ultrasound images.

The ultrasound diagnosis method further includes receiving an input related to first information from a user onto the first ultrasound image.

The ultrasound diagnosis method further includes performing at least one of operations for adding, moving, and deleting at least one of the nodes and the trunk lines based on the received input.

The obtaining of the second ultrasound images includes receiving an input for selecting at least one node from among the nodes from a user; and automatically obtaining second ultrasound images based on the selected node(s).

The obtaining of the second ultrasound images includes receiving an input for selecting at least one node from among the nodes from a user; and automatically obtaining second ultrasound images based on nodes other than the selected node(s).

The ultrasound diagnosis method further includes receiving an input related to a sequence of nodes regarding at least two from among the nodes from a user, and moving a viewpoint based on the received input related to the sequence of nodes and obtaining second ultrasound images.

The ultrasound diagnosis method further includes receiving an input related to a speed of moving a viewpoint between nodes from a user, and moving the viewpoint based on the speed of moving a viewpoint and obtaining the second ultrasound images.

The input related to a speed of moving a viewpoint includes moving time between nodes.

The obtaining of the first ultrasound image includes extracting first information including the nodes and the trunk lines from the ultrasound image by performing an image processing including a centerline extracting algorithm.

The obtaining of the second ultrasound images includes moving a viewpoint based on the first information and automatically obtaining the second ultrasound images.

The obtaining of the second ultrasound images includes moving a viewpoint along trunk lines between the nodes and obtaining second ultrasound images.

The ultrasound diagnosis method further includes displaying at least one of the nodes and the trunk lines passed by a viewpoint.

The displaying of at least one of the nodes and the trunk lines passed by the viewpoint includes displaying at least one from among the nodes and the trunk lines passed by a viewpoint in a transparency, a color, or a shape different from the nodes and the trunk lines not passed by the viewpoint.

According to one or more exemplary embodiments, an ultrasound diagnosis method includes obtaining ultrasound data by scanning a target object; receiving an input from a user; obtaining first information including a plurality of nodes based on the ultrasound data; and moving a viewpoint based on the first information and the received input and obtaining ultrasound images.

According to one or more exemplary embodiments, an ultrasound diagnosis method includes obtaining ultrasound data by scanning a target object; obtaining first information including at least one of a plurality of nodes and a plurality of trunk lines based on the ultrasound data; moving a viewpoint based on the first information; and displaying first information passed by the viewpoint to be distinguishable from first information not passed by the viewpoint.

According to one or more exemplary embodiments, an ultrasound diagnosis method includes obtaining a first ultrasound image by scanning a target object; receiving an input from a user; obtaining first information including a plurality of nodes included in the first ultrasound image based on the received input; obtaining a sequence of the nodes based on the received input; and moving a viewpoint based on the sequence of nodes and the first information and obtaining second ultrasound images.

According to one or more exemplary embodiments, there is provided a computer readable recording medium having recorded thereon a computer program for implementing an ultrasound diagnosis method as described above.

BRIEF DESCRIPTION OF THE DRAWINGS

These and/or other aspects will become apparent and more readily appreciated from the following description of the embodiments, taken in conjunction with the accompanying drawings in which.

DETAILED DESCRIPTION

Figure 1:
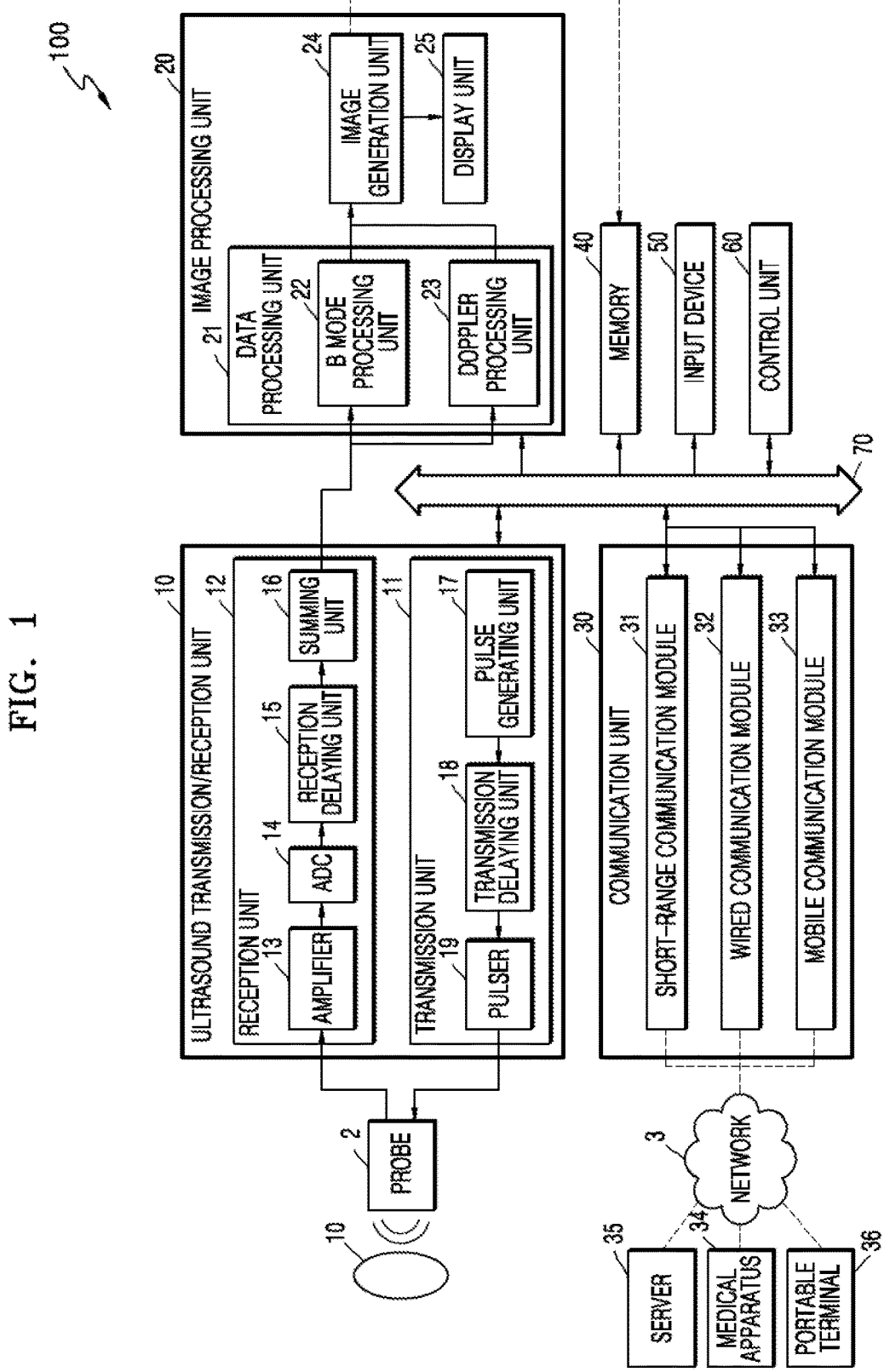
FIG. 1 is a diagram illustrating an ultrasound imaging apparatus according to exemplary embodiments.

Reference will now be made in detail to exemplary embodiments, examples of which are illustrated in the accompanying drawings, wherein like reference numerals refer to like elements throughout. In this regard, the present exemplary embodiments may have different forms and should not be construed as being limited to the descriptions set forth herein. Accordingly, the exemplary embodiments are merely described below, by referring to the figures, to explain aspects of the present description. As used herein, expressions such as "at least one of," when preceding a list of elements, modify the entire list of elements and do not modify the individual elements of the list.

The terms used in this specification are those general terms currently widely used in the art in consideration of functions in regard to the inventive concept, but the terms may vary according to the intention of those of ordinary skill in the art, precedents, or new technology in the art. Also, specified terms may be selected by the applicant, and in this case, the detailed meaning thereof will be described in the detailed description of the inventive concept. Thus, the terms used in the specification should be understood not as simple names but based on the meaning of the terms and the overall description of the inventive concept.

When something "comprises" or "includes" a component, another component may be further included unless specified otherwise. Also, the terms "unit" and "module" used herein represent a unit for processing at least one function or operation, which may be implemented by hardware, software, or a combination of hardware and software.

Throughout the specification, an "ultrasound image" refers to an image of an object acquired by using an ultrasonic wave. Also, an "object" may include a person or an animal, or a part of a person or an animal. For example, the object may include an organ such as a liver, a heart, a womb, a brain, a breast, or an abdomen, or a blood vessel. Also, the object may include a phantom. The phantom may refer to a material having a volume that is approximately the intensity and effective atomic number of a living thing, and may include a spherical phantom having a property similar to a human body.

Also, a "user" may be, but is not limited to, a medical expert such as a doctor, a nurse, a medical laboratory technologist, a medial image expert, or a technician who repairs a medical apparatus.

Hereinafter, exemplary embodiments will be described in detail with reference to the accompanying drawings.

FIG. 1 is a diagram illustrating an ultrasound imaging apparatus according to exemplary embodiments.

FIG. 1 illustrates an overall configuration of an ultrasound diagnosis apparatus 100 according to exemplary embodiments.

Referring to FIG. 1, the ultrasound diagnosis apparatus 100 may include a probe 2, an ultrasound transmission/reception unit 10, an image processing unit 20, a communication unit 30, a memory 40, an input device 50, and a control unit 60, where the components stated above may be connected to one another via buses 70.

The ultrasound diagnosis apparatus 100 may be embodied not only as a cart type apparatus, but also as a portable apparatus. Examples of portable ultrasound diagnosis apparatuses may include a picture archiving and communication system (PACS) viewer, a smart phone, a laptop computer, a personal digital assistant (PDA), and a tablet personal computer (PC); however, the inventive concept is not limited thereto.

The probe 2 transmits an ultrasound signal to an object 1 according to a driving signal applied from the ultrasound transmission/reception unit 10 and receives an echo signal reflected from the object 1. The probe 2 includes a plurality of transducers, and the plurality of transducers oscillate according to an electrical signal transmitted thereto and generate an ultrasound wave, that is, acoustic energy. Also, the probe 2 may be connected to a main body of the ultrasound diagnosis apparatus 100 by wire or wirelessly, and the ultrasound diagnosis apparatus 100 may include a plurality of probes 2.

A transmission unit 11 supplies a driving signal to the probe 2 and includes a pulse generating unit 17, a transmission delaying unit 18, and a pulser 19. The pulse generating unit 17 generates pulses for forming transmission ultrasound waves according to a predetermined pulse repetition frequency (PRF), and the transmission delaying unit 18 applies a delay time for determining transmission directionality to the pulses. The pulses to which a delay time is applied correspond to a plurality of piezoelectric vibrators included in the probe 2, respectively. The pulser 19 applies a driving signal (or a driving pulse) to the probe 2 at a timing corresponding to each pulse to which a delay time is applied.

A reception unit 12 generates ultrasound data by processing echo signals received from the probe 2 and may include an amplifier 13, an analog-digital converter (ADC) 14, a reception delaying unit 15, and a summing unit 16. The amplifier 13 amplifies echo signals in each channel, and the ADC 14 analog-to-digital converts the amplified echo signals. The reception delaying unit 15 applies delay times for determining reception directionality to the digital-converted echo signals, and the summing unit 16 generates ultrasound data by summing the echo signals processed by the reception delaying unit 15. Also, according to exemplary embodiments, the reception unit 12 may not include the amplifier 13. In other words, when the sensitivity of the probe 2 or the capability to process bits by the ADC 14 is enhanced, the amplifier 13 may be omitted.

The image processing unit 20 generates an ultrasound image by scan-converting ultrasound data generated by the ultrasound transmission/reception unit 10 and displays the ultrasound image. The ultrasound image may include not only a gray-scale image obtained by scanning the object 1 in an amplitude (A) mode, a brightness (B) mode, and a motion (M) mode, but also a Doppler image representing a motion of the object 1 by using a Doppler effect. The Doppler image may include a bloodstream Doppler image (also referred to as a color Doppler image) representing a flow of blood, a tissue Doppler image representing a motion of a tissue, and a spectral Doppler image representing a movement speed of the object 1 in a waveform.

A B mode processing unit 22 extracts B mode components from ultrasound data and processes the B mode components. An image generating unit 24 may generate an ultrasound image representing signal intensities as brightness, based on the B mode components extracted by the B mode processing unit 22.

Likewise, a Doppler processing unit 23 may extract Doppler components from ultrasound data, and the image generating unit 24 may generate a Doppler image representing a motion of the object 1 as colors or waveforms based on the extracted Doppler components.

The image generating unit 24 according to an exemplary embodiment may generate a three-dimensional 3D) ultrasound image through volume-rendering of volume data and may also generate an elasticity image that visualizes the deformation of the object 1 due to a pressure. In addition, the image generating unit 24 may display various additional information in an ultrasound image by using texts and graphics. The generated ultrasound image may be stored in the memory 40.

A display unit 25 displays the generated ultrasound image. The display unit 25 may display not only an ultrasound image, but also various information processed by the ultrasound diagnosis apparatus 100 on a screen via a graphic user interface (GUI). The ultrasound diagnosis apparatus 100 may include two or more display units 25 according to exemplary embodiments.

The communication unit 30 is connected by wire or wirelessly to a network 3 to communicate with an external device or a server. The communication unit 30 may exchange data with a hospital server or other medical apparatuses in a hospital connected through a Picture Archiving and Communication System (PACS). Also, the communication unit 30 may perform data communication according to the Digital Imaging and Communications in Medicine (DICOM) standard.

The communication unit 30 may transmit and receive data related to diagnosis of the object 1, e.g., an ultrasound image, ultrasound data, and Doppler data of the object 1, via the network 3 and may also transmit and receive medical images obtained by other medical apparatuses, e.g., a computer tomography (CT) image, a magnetic resonance imaging (MRI) image, and an X-ray image. In addition, the communication unit 30 may receive information related to a diagnosis history or treatment schedule of a patient from a server and use the information to diagnose the object 1. In addition, the communication unit 30 may perform data communication not only with a server or a medical apparatus in a hospital, but also with a portable terminal of a doctor or a patient.

The communication unit 30 may be connected by wire or wirelessly to the network 3 to exchange data with a server 35, a medical apparatus 34, or a portable terminal 36. The communication unit 30 may include one or more components that enable communication with external devices, and may include, for example, a short-range communication module 31, a wired communication module 32, and a mobile communication module 33.

The short-range communication module 31 refers to a module for short-range communication within a predetermined distance. Examples of short-range communication techniques according to an exemplary embodiment may include wireless LAN, Wi-Fi, Bluetooth, Zigbee, Wi-Fi Direct (WFD), ultra wideband (UWB), infrared data association (IrDA), Bluetooth Low Energy (BLE), and near field communication (NFC); however, the inventive concept is not limited thereto.

The wired communication module 32 refers to a module for communication using electrical signals or optical signals. Examples of wired communication techniques according to an exemplary embodiment may include a twisted pair cable, a coaxial cable, an optical fiber cable, and an Ethernet cable.

The mobile communication module 33 transmits and receives wireless signals to and from at least one of a base station, an external terminal, and a server on a mobile communication network. Herein, the wireless signals may include voice call signals, video call signals, or various types of data for transmission and reception of text/multimedia messages.

The memory 40 stores various data processed by the ultrasound diagnosis apparatus 100. For example, the memory 40 may store medical data related to diagnosis of the object 1, such as ultrasound data and ultrasound images that are input or output and may also store algorithms or programs to be executed in the ultrasound diagnosis apparatus 100.

The memory 40 may be embodied as any of various storage media such as a flash memory, a hard disk drive, and an electrically erasable programmable read-only memory (EEPROM). Also, the ultrasound diagnosis apparatus 100 may utilize web storage or a cloud server that functions as the memory 40 online.

The input device 50 refers to a unit via which a user inputs data for controlling the ultrasound diagnosis apparatus 100.

The input device 50 may include hardware components, such as a keypad, a mouse, a touch panel, a touch screen, a track ball, and a jog switch. However, the inventive concept is not limited thereto, and the input device 50 may further include various other input units, such as an electrocardiogram measuring module, a respiration measuring module, a voice recognition sensor, a gesture recognition sensor, a fingerprint recognition sensor, an iris recognition sensor, a depth sensor, and a distance sensor.

The control unit 60 may control overall operations of the ultrasonic diagnosis apparatus 100. In other words, the control unit 60 may control operations among the probe 2, the ultrasound transmission/reception unit 10, the image processing unit 20, the communication unit 30, the memory 40, and the input device 50 illustrated in FIG. 1.

All or some of the probe 2, the ultrasound transmission/reception unit 10, the image processing unit 20, the communication unit 30, the memory 40, the input device 50, and the control unit 60 may be operated by software modules. However, the inventive concept is not limited thereto, and some of the above components may be operated by hardware modules. Also, at least one of the ultrasound transmission/reception unit 10, the image processing unit 20, and the communication unit 30 may be included in the control unit 60; however, the inventive concept is not limited thereto.

For diagnosis of a disease by using an ultrasound image, a marker may be set to indicate a predetermined position or set a diagnosis region in an ultrasound image including an object.

In detail, the marker may be set at a portion that is to be observed in detail by the user to diagnose a disease or to check the health of a patient. The inventive concept provides an ultrasound diagnosis apparatus and an ultrasound image display method, which may change and output an ultrasound image to more accurately diagnose an object region in which the marker is set.

Figure 2:
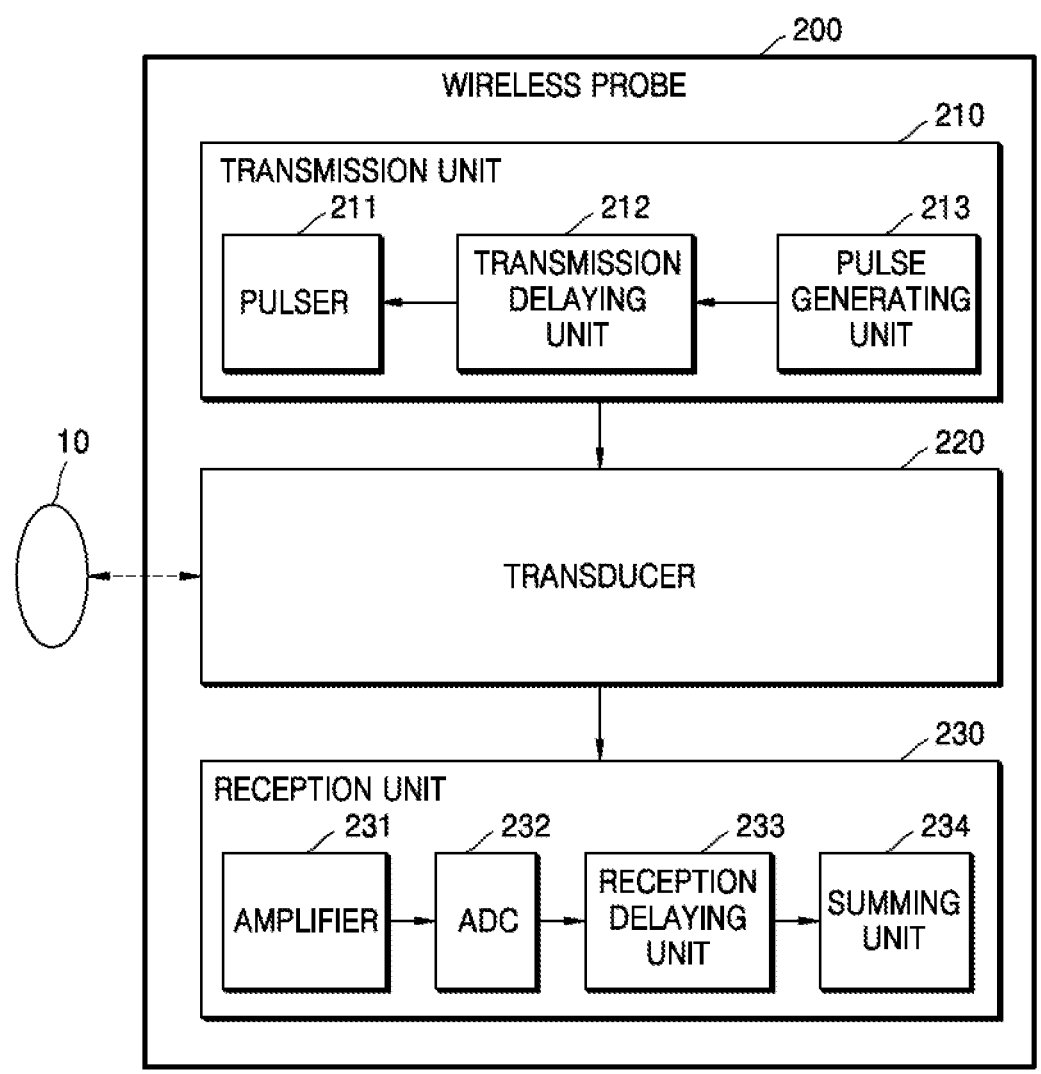
FIG. 2 is a block diagram illustrating a configuration of a wireless probe 200 according to an exemplary embodiment.

FIG. 2 is a block diagram illustrating a configuration of a wireless probe 200 according to an exemplary embodiment.

The wireless probe 200 may include a plurality of transducers as described with reference to FIG. 1, and may include some or all of the configurations of the ultrasound transmission/reception unit 10 of FIG. 1 according to exemplary embodiments.

The wireless probe 200 according to the exemplary embodiment illustrated in FIG. 2 may include a transmission unit 210, a transducer 220, and a reception unit 230, and detailed descriptions of the respective components will be omitted since they have already been described with reference to FIG. 1. The wireless probe 200 may include a reception delaying unit 233 and a summing unit 234 selectively according to exemplary embodiments.

The wireless probe 200 may transmit an ultrasound signal to the object 1 and receive an echo signal therefrom, and may generate ultrasound data and wirelessly transmit the ultrasound data to the ultrasound diagnosis apparatus 100 of FIG. 1.

When a user performs an ultrasound diagnosis with respect to a tubular target object, such as a blood vessel and a digestive system, by using a ultrasound diagnosis apparatus as described above, it may be necessary to move a viewpoint to each of a plurality of terminal ends of the target object in turn. Here, a viewpoint corresponds to a designated location for obtaining an ultrasound image. In a current ultrasound diagnosis apparatus, a viewpoint is moved by using a trackball. However, it is inconvenient for a user to move a viewpoint using a trackball one after another.

Furthermore, a user is unable to recognize a path in which a viewpoint is moved after the viewpoint is moved.

Hereinafter, referring to FIGS. 3 through 17, an ultrasound diagnosis apparatus and an ultrasound diagnosis method for easily moving viewpoints and a computer readable recording medium having recorded thereon a computer program for implementing the method according to an embodiment will be described in detail.

An ultrasound diagnosis apparatus may create an ultrasound image by obtaining signals from a probe and measure a length, an angle, an area, and a volume of a particular organ or a particular structure in the ultrasound image. Based on the measurement, information regarding abnormal region in a human body or information regarding gestational age may be obtained. An ultrasound diagnosis apparatus is an important tool frequently used for aiding a medical diagnosis, and thus convenience of usage and accuracy are demanded.

Here, to improve efficiency of a medical diagnosis, it is necessary to provide a method that enables a user, such as a doctor, to easily move a viewpoint on a ultrasound image using an input device.

Figure 3:
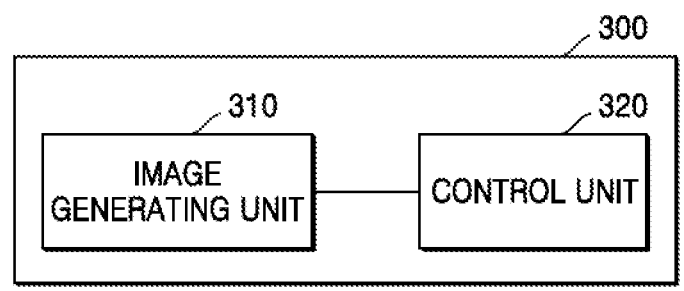
FIG. 3 is a diagram showing a ultrasound diagnosis apparatus 300 according to an embodiment.

FIG. 3 is a diagram showing a ultrasound diagnosis apparatus 300 according to an embodiment.

Referring to FIG. 3, the ultrasound diagnosis apparatus 300 according to an embodiment includes an image generating unit 310 and a control unit 320.

The ultrasound diagnosis apparatus 300 may be any electronic device capable of generating and processing an ultrasound image and may correspond to the ultrasound diagnosis apparatus 100 as shown in FIG. 1. Furthermore, the ultrasound diagnosis apparatus 300 may be the server 35, the medical apparatus 34, or the terminal 36 that may be connected to the ultrasound diagnosis apparatus 100 shown in FIG. 1 via the network 3. Furthermore, the image generating unit 310 and the control unit 320 of FIG. 3 correspond to the image generating unit 24 and the control unit 60 of FIG. 1, and thus descriptions identical to those given above with reference to FIG. 1 will be omitted.

The image generating unit 310 obtains a first ultrasound image based on ultrasound data obtained by scanning a target object. Furthermore, the control unit 320 obtains first information including a plurality of nodes based on the ultrasound data and moves a viewpoint based on the first information and obtain second ultrasound images.

Ultrasound data may be obtained by an ultrasound data obtaining unit. Furthermore, the ultrasound data obtaining unit may obtain ultrasound data by scanning a target object using ultrasound signals. However, the inventive concept is not limited thereto. For example, the ultrasound data obtaining unit may correspond to the ultrasound transmission/reception unit 10 shown in FIG. 1, may receive ultrasound echo signals transmitted from the probe 2, and may autonomously obtain ultrasound data by using the received ultrasound echo signals. Furthermore, the ultrasound data obtaining unit may correspond to the wireless probe 200 of FIG. 2. The ultrasound data obtaining unit may receive ultrasound echo signals transmitted by the wireless probe 200 and autonomously obtain ultrasound data by using the received ultrasound echo signals.

For another example, the ultrasound data obtaining unit may receive ultrasound data from an external device. For example, the ultrasound data obtaining unit may receive ultrasound data from the network 3 of FIG. 1. However, the inventive concept is not limited thereto, and the ultrasound diagnosis apparatus 300 may obtain ultrasound image data using any of various other methods.

Furthermore, the control unit 320 may obtain trunk lines interconnecting nodes and may obtain a structure included in a first ultrasound image based on a plurality of nodes and the trunk line. Furthermore, first information may include at least one of trunk lines and a structure. Furthermore, the ultrasound diagnosis apparatus 300 may obtain a sequence of nodes in the order that viewpoint is moved and may obtain an ultrasound image based on the sequence of the nodes and the first information when a viewpoint is moved.

A node is a nodal point at a particular location, and a node may be connected to another node via a trunk line. A node may be a branch node, a leaf node, and a path node. A leaf node is a node connected to another node via a trunk line. A path node is a node connected to two other nodes via trunk lines. Furthermore, a branch node is a node connected to three or more other nodes via trunk lines. A structure may be a graph including nodes and trunk lines. A graph refers to a drawing consisting of nodes and trunk lines indicating relationships between the nodes. Furthermore, a structure may have a shape formed by nodes and trunk lines in correspondence to that of a target object. For example, if a target object is a heart including a blood vessel, a structure may be a blood vessel structure having a shape identical or similar to that of an actual blood vessel, such that a user may easily recognize blood vessel shape. Furthermore, nodes may be included in an image of a target object, and a display unit may display the image together with an ultrasound image.

According to another embodiment, a node may be obtained based on ultrasound data. For example, the ultrasound diagnosis apparatus 300 may extract at least one of nodes and trunk lines from ultrasound data using a centerline extracting algorithm. The ultrasound diagnosis apparatus 300 may obtain an ultrasound image based on at least one of nodes and trunk lines. For example, the ultrasound diagnosis apparatus 300 may obtain at least one of nodes and trunk lines as a viewpoint and obtain an ultrasound image viewed from the viewpoint.

Figure 18:
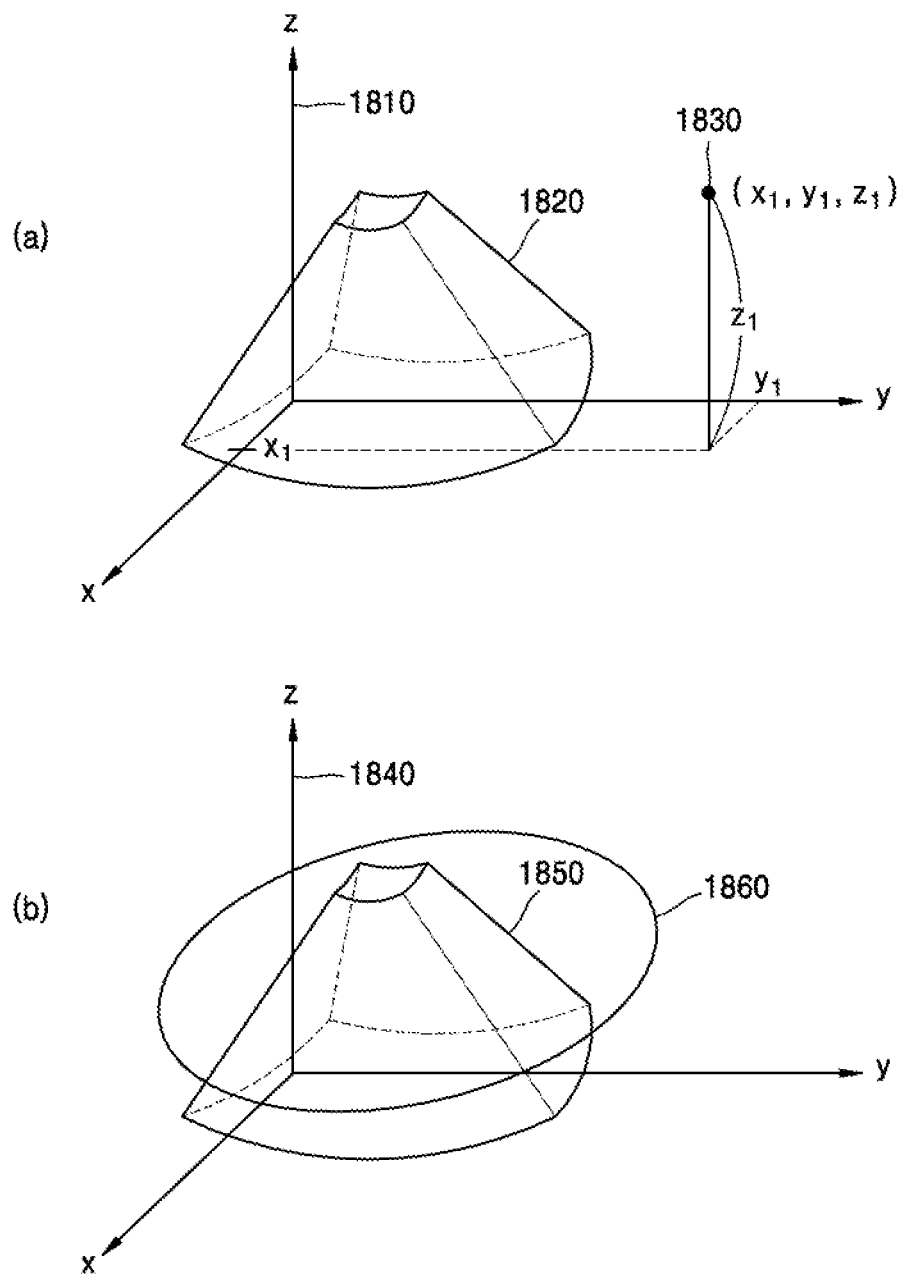

Furthermore, according to another embodiment, referring to FIG. 18(*a*), ultrasound data 1820 may be data on a coordinate system 1810. The coordinate system 1810 may include at least one from among an orthogonal coordinate system, a cylindrical coordinate system, and a circular coordinate system. FIG. 18(*a*) exemplifies a case in which the coordinate system 1810 is an orthogonal coordinate system. The control unit 320 may locate a node 1830 at a location a designated distance apart from the ultrasound data 1820. For example, the control unit 320 may locate a node at a coordinate (x1, y1, z1. Furthermore, the ultrasound diagnosis apparatus 300 may obtain an ultrasound image based on the node. For example, the ultrasound diagnosis apparatus 300 may obtain a node as a viewpoint and obtain an ultrasound image viewed from the viewpoint based on the ultrasound data 1820. In this case, the node may not be included in the ultrasound image.

Furthermore, although the above descriptions are given with respect to nodes, the inventive concept is not limited thereto. For example, ultrasound data 1850 may be data on a coordinate system 1840. The ultrasound diagnosis apparatus 300 may locate an orbit 1860 at a location a designated distance apart from the ultrasound data 1850. Furthermore, the ultrasound diagnosis apparatus 300 may obtain an ultrasound image based on the orbit. For example, the ultrasound diagnosis apparatus 300 may obtain an ultrasound image viewed from the orbit based on the ultrasound data 1850.

An ultrasound image may include a first ultrasound image and a second ultrasound image. A first ultrasound image is an image obtained based on ultrasound data obtained by ultrasound scanning a target object. In detail, a first ultrasound image is an ultrasound image of a target object used by a user to determining a region to observe. A first ultrasound image may be at least one of a 2D cross-sectional ultrasound image and a 3D-rendered endoscopic image. Furthermore, a second ultrasound image is an ultrasound image obtained by an ultrasound diagnosis apparatus for a user to observe an ultrasound image of a target object. In detail, a second ultrasound image may be an ultrasound image showing a designated portion of a first ultrasound image in closer details.

For another example, a second ultrasound image may be an ultrasound image showing a section of a designated portion of a first ultrasound image. A user may observe a first ultrasound image, which is an ultrasound image of a target object, determine a portion to observe on the first ultrasound image, and observe a second ultrasound image corresponding to the determination. Therefore, a first ultrasound image and a second ultrasound image may be actually displayed on a same display screen. However, the inventive concept is not limited thereto, and a first ultrasound image and a second ultrasound image may be displayed on different display screens for convenience of a user. For example, a first ultrasound image may be displayed at a designated portion of a second ultrasound image as a mini ultrasound image. A first ultrasound image may be an image showing an entire ultrasound image regarding a target object. A second ultrasound image may be a screen image magnifying a designated portion of a first ultrasound image. A first ultrasound image may be displayed at a designated portion of a second ultrasound image, and thus a user may determine which portion of a first ultrasound image is magnified in a second ultrasound image based on an entire image shown in the first ultrasound image.

Furthermore, a second ultrasound image may be an image that is 2-dimensionally or 3-dimensionally represented by image processing a first ultrasound image. Furthermore, a second ultrasound image may include a virtual endoscopic image based on ultrasound data. Therefore, a user may easily perform a sketchy endoscopic diagnosis on a target object using an ultrasound diagnosis apparatus without performing an actual endoscopic diagnosis. In the present embodiment, a first ultrasound image and a second ultrasound image are separately stated if it is necessary to differentiate one from another. However, if it is not necessary to differentiate, an ultrasound image including a first ultrasound image and a second ultrasound image is stated.

The control unit 320 may obtain nodes and trunk lines from a first ultrasound image, obtain viewpoints at the nodes and the trunk line of the first ultrasound image, and provide a second ultrasound image to a user. According to the inventive concept, a viewpoint may be automatically moved along nodes and trunk lines. In detail, the control unit 320 may move a viewpoint of an ultrasound image in a particular direction or according to pre-set rules. Therefore, it is not necessary for a user to move a viewpoint by using a trackball.

Figure 4:
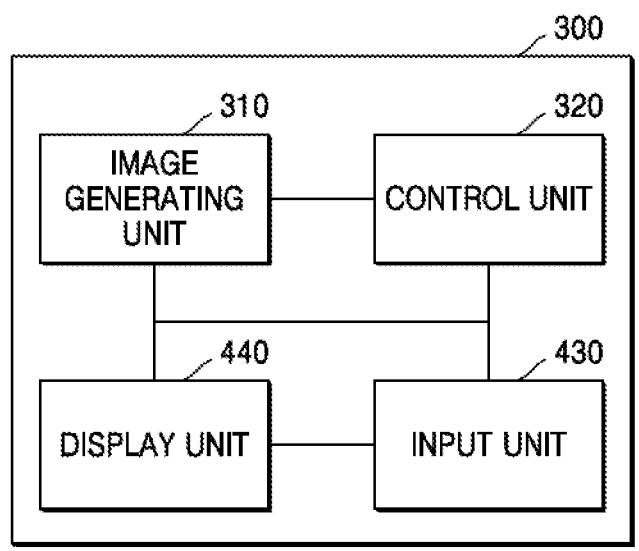
FIG. 4 is a diagram showing a ultrasound diagnosis apparatus 300 according to another embodiment.

FIG. 4 is a diagram showing a ultrasound diagnosis apparatus 300 according to another embodiment.

Referring to FIG. 4, the ultrasound diagnosis apparatus 300 according to another embodiment includes an image generating unit 310, a control unit 320, an input unit 430, and a display unit 440. Since the image generating unit 310 and the control unit 320 included in the ultrasound diagnosis apparatus 300 are identical to the image generating unit 310 and the control unit 320 described above with reference to FIG. 3, descriptions thereof will be omitted, and descriptions of the input unit 430 and the display unit 440 will be given below.

The input unit 430 may be identical to the input device 50 of FIG. 1, and thus description identical to the description of the input device 50 given above will be omitted. The input unit 430 may receive a user input from a user via a user interface screen image including a first ultrasound image. The input unit 430 may correspond to the input device 50. For example, the input unit 430 may be formed as a touch screen and may receive a user input via a user interface screen image including a first ultrasound image displayed on the touch screen. Based on a user input received by the input unit 430, the control unit 320 may obtain nodes and trunk lines from a first ultrasound image, obtain viewpoints at the nodes and the trunk line on the first ultrasound image, and provide a second ultrasound image to a user. The input unit 430 may receive a viewpoint moving input from a user. For example, if the input unit 430 includes a mouse, a user may move a viewpoint between nodes by clicking the nodes using the mouse, which is the input unit 430.

Furthermore, based on an input received by the input unit 430, the control unit 320 may obtain a sequence of nodes. The control unit 320 may move a viewpoint based on the sequence of the nodes and obtain an ultrasound image.

The display unit 440 may correspond to the display unit 25 of FIG. 1, and thus descriptions thereof already given above with reference to FIG. 1 will be omitted. The display unit 440 displays a designated screen image under the control of the input unit 430. In detail, the display unit 440 includes a display panel (not shown) and may display a user interface screen image or a medical image screen image including an ultrasound image or the like on the display panel. The display unit 440 may display a first ultrasound image and a second ultrasound image. Furthermore, the control unit 320 may obtain second information indicating at least one of a location and a direction of a viewpoint based on first information. The display unit 440 may display an image in which at least one of first information and second information is displayed on a first ultrasound image. Here, a direction of a viewpoint refers to a direction at a designated location for obtaining an ultrasound image.

Furthermore, according to another embodiment, the ultrasound diagnosis apparatus 300 may include an image generating unit 310, a control unit 320, and an input unit 430. The image generating unit 310 may obtain a first ultrasound image by scanning a target object. Furthermore, the input unit 430 may receive an input from a user. Furthermore, the control unit 320 may obtain first information including a plurality of nodes included in the first ultrasound image and may move a viewpoint based on the first information and the received input and obtain second ultrasound images.

Furthermore, according to another embodiment, the ultrasound diagnosis apparatus 300 may include an image generating unit 310, a control unit 320, and an input unit 430. The image generating unit 310 may obtain a first ultrasound image by scanning a target object. The control unit 320 may obtain first information including at least one of a plurality of nodes and trunk lines included in the first ultrasound image and may move a viewpoint based on the first information and obtain second ultrasound images. Furthermore, the display unit 440 may display first information passed by the viewpoint to be distinguishable from first information not yet passed by the viewpoint. The display unit 440 may use different shapes, different colors, different transparencies, different animation effects, or different texts to display first information passed by the viewpoint to be distinguishable from first information not yet passed by the viewpoint.

Furthermore, according to another embodiment, the ultrasound diagnosis apparatus 300 may include an image generating unit 310, a control unit 320, and an input unit 430. The image generating unit 310 may obtain a first ultrasound image by scanning a target object. The input unit 430 may receive an input from a user. The control unit 320 may obtain first information including a plurality of nodes included in the first ultrasound image, obtain a sequence of the nodes based on the received input, and move a viewpoint based on the sequence of the nodes and obtain second ultrasound images.

Figure 5:
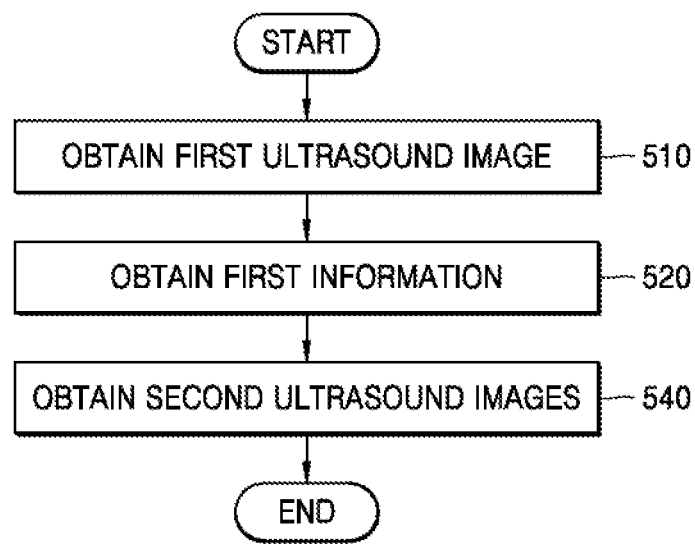
FIG. 5 is a diagram showing an ultrasound diagnosis method according to an embodiment.

FIG. 5 is a diagram showing an ultrasound diagnosis method according to an embodiment.

Referring to FIG. 5, the ultrasound diagnosis method according to an embodiment may include an operation 510 for obtaining a first ultrasound image, an operation 520 for obtaining first information, and an operation 540 for obtaining second ultrasound images. An ultrasound diagnosis method according to an embodiment may be performed by the ultrasound diagnosis apparatus 300 according to the embodiments described above with reference to FIGS. 3 and 4. Hereinafter, the ultrasound diagnosis method according to an embodiment will be described in relation to the ultrasound diagnosis apparatus 300 in FIG. 4. Furthermore, detailed description of the ultrasound diagnosis method according to an embodiment will be given below except descriptions identical to the descriptions of the ultrasound diagnosis apparatus 300 given above with reference to FIGS. 3 and 4 will be omitted.

The operation 510 for obtaining a first ultrasound image is an operation in which ultrasound data is obtained by scanning a target object and the image generating unit 310 obtains a first ultrasound image based on the ultrasound data. The operation 510 may be performed as the ultrasound diagnosis apparatus 300 externally receives or autonomously generates a first ultrasound image obtained based on ultrasound data transmitted via the probe 2. The operation 520 for obtaining first information is an operation in which the control unit 320 obtains first information including a plurality of nodes based on the ultrasound data. The operation 520 may be performed by the control unit 320. Furthermore, the control unit 320 may perform an operation for moving a viewpoint based on the first information and obtaining second ultrasound images.

The control unit 320 may perform an operation for obtaining second information indicating at least one of a location and a direction of a viewpoint based on the first information. Furthermore, under the control of the control unit 320, the display unit 440 may perform an operation for displaying at least one of the first information and the second information on the first ultrasound image.

The control unit 320 may perform an operation for obtaining trunk lines interconnecting nodes and an operation for obtaining a structure included in the first ultrasound image based on a plurality of nodes and trunk lines. The first information may include at least one of trunk lines and a structure.

The operation 540 for obtaining the second ultrasound images may include an operation (not shown) for automatically obtaining a sequence of at least two nodes from among a plurality of nodes; and an operation (not shown) in which the image generating unit 310 moves a viewpoint according to the obtained sequence of the nodes and obtains second ultrasound images.

The input unit 430 may perform an operation for receiving an input related to the first information from a user onto the first ultrasound image.

The control unit 320 may perform an operation for performing adding, moving, or deleting at least one of the nodes and the trunk line based on the received input.

The operation 540 for obtaining the second ultrasound images may include an operation for receiving an input for selecting at least one node from among the nodes from a user and an operation for automatically obtaining the second ultrasound images based on the selected node(s).

The operation for obtaining the second ultrasound images may include an operation for receiving an input for selecting at least one node from among the nodes from a user and an operation for automatically obtaining the second ultrasound images based on nodes other than the selected node(s).

The input unit 430 may perform an operation for receiving an input related to a sequence of at least two nodes from among the nodes from a user. The control unit 320 may perform an operation for moving a viewpoint based on the received input related to the sequence of the nodes and obtaining the second ultrasound images.

The input unit 430 may perform an operation for receiving an input related to a speed of movement between nodes from a user. The control unit 320 may perform an operation for obtaining the second ultrasound images by moving a viewpoint based on the speed of movement. Furthermore, the input related to the speed of movement may include moving times between nodes. Therefore, a user may set moving times between nodes, so that the user may move a viewpoint slowly at a region for detailed observation.

The operation for obtaining the first information may include an operation for extracting first information including nodes and trunk lines from an ultrasound image by using an image processing including a centerline extracting algorithm.

The operation for obtaining the second ultrasound images may include an operation for moving a viewpoint based on the extracted first information and automatically obtaining the second ultrasound images.

The operation for obtaining the second ultrasound images may include an operation for moving a viewpoint along trunk lines between nodes and obtaining the second ultrasound images.

The display unit 440 may perform an operation for displaying at least one of nodes and trunk lines that are passed by the viewpoint to obtain images.

Furthermore, the display unit 440 may perform an operation for displaying at least one of nodes and trunk lines passed by a viewpoint in at least one of a transparency, a color, and a shape different from nodes and trunk lines not passed by the viewpoint. For example, nodes and trunk lines not passed by a viewpoint may be displayed more transparently than nodes and trunk lines passed by the viewpoint. Furthermore, nodes and trunk lines not passed by a viewpoint may be displayed in colors different from nodes and trunk lines passed by the viewpoint. Furthermore, nodes not passed by a viewpoint may be displayed as triangles, whereas nodes passed by the viewpoint may be displayed as circles. Furthermore, nodes and trunk lines not passed by a viewpoint may be displayed using animation effects different from nodes and trunk lines passed by the viewpoint.

An ultrasound diagnosis method according to another embodiment may include an operation in which an ultrasound data obtaining unit (not shown) obtains ultrasound data by scanning a target object. Furthermore, the input unit 430 may receive an input from a user. Furthermore, the control unit 320 may obtain first information including a plurality of nodes based on the ultrasound data and may obtain an ultrasound image by moving a viewpoint based on the first information and the received input.

An ultrasound diagnosis method according to another embodiment may include an operation in which an ultrasound data obtaining unit (not shown) obtains ultrasound data by scanning a target object. Furthermore, the control unit 320 may obtain first information including at least one of a plurality of nodes and trunk lines based on the ultrasound data and move a viewpoint based on the first information. Furthermore, the display unit 440 may display first information passed by the viewpoint to be distinguishable from first information not passed by the viewpoint. The display unit 440 may use different shapes, colors, transparencies, animation effects, or texts to distinguish the first information passed by the viewpoint from the first information not passed by the viewpoint.

An ultrasound diagnosis method according to another embodiment may include an operation in which an ultrasound data obtaining unit (not shown) obtains a first ultrasound image by scanning a target object. Furthermore, the input unit 430 may receive an input from a user. Furthermore, the control unit 320 may obtain first information including a plurality of nodes included in the first ultrasound image based on the received input and obtain a sequence of nodes based on the received input. Furthermore, second ultrasound images may be obtained by moving an viewpoint based on the first information and the sequence of the nodes.

Furthermore, a computer readable recording medium having recorded thereon a computer program for implementing the method described above with reference to FIG. 5 may be provided.

Figure 6:
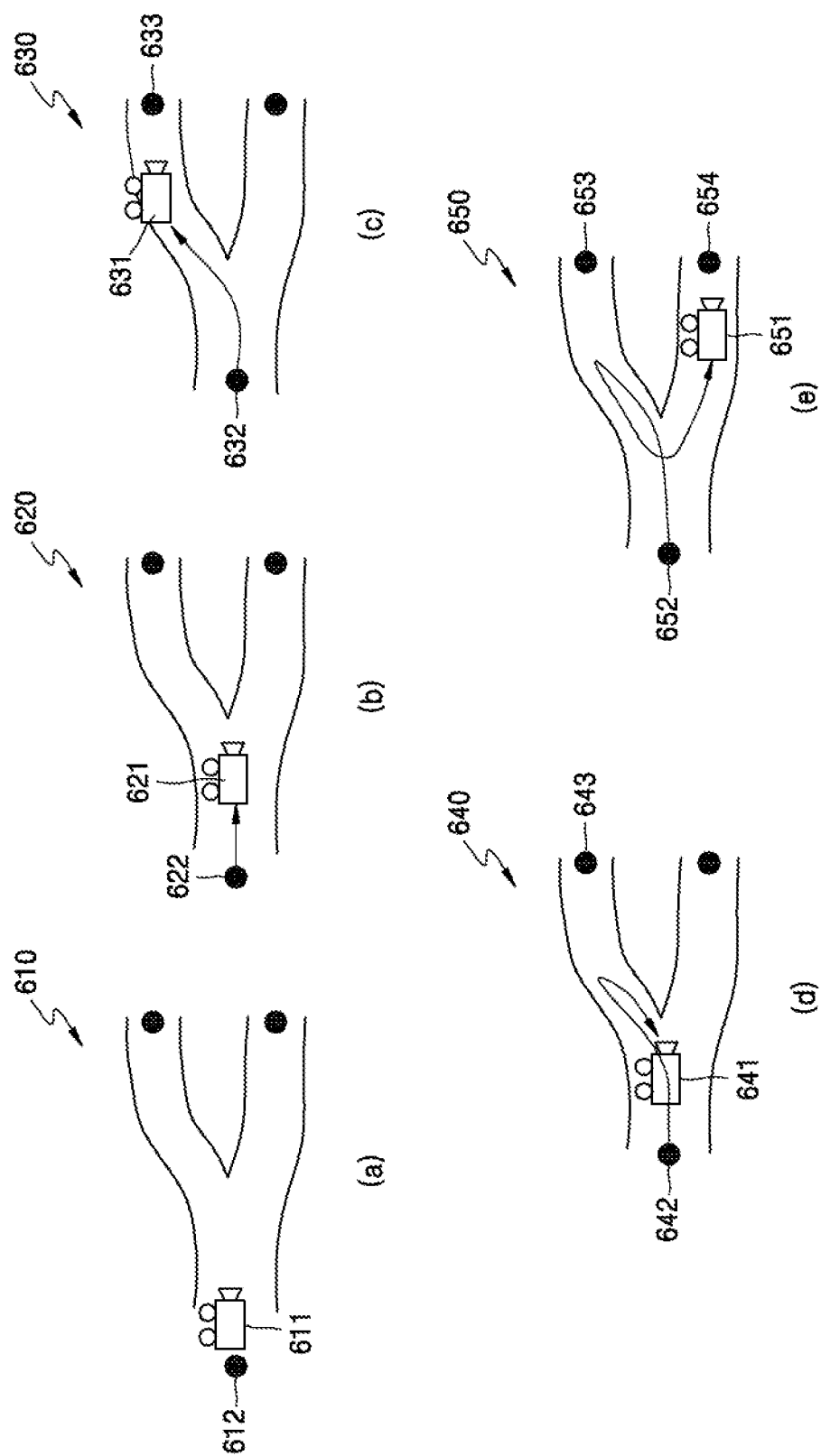
FIG. 6 is a diagram for describing movement of a viewpoint on an ultrasound image at an ultrasound diagnosis apparatus in the related art.

FIG. 6 is a diagram for describing movement of a viewpoint on an ultrasound image at an ultrasound diagnosis apparatus in the related art.

Referring to FIG. 6, it is difficult for a user to move a viewpoint to observe a region of interest at an ultrasound diagnosis apparatus in the related art. In case of a general ultrasound diagnosis apparatus, a viewpoint of an ultrasound image is adjusted in correspondence to a user input that is input via a trackball. For diagnosis of a target object, it is necessary for a user to observe the target object by moving a viewpoint of an ultrasound image. Hereinafter, a case in which a user moves a viewpoint by using a trackball will be described. For example, a process for a user to observe a point 653 and a point 654 on an ultrasound image 650 of FIG. 6 will be described below. Referring to FIG. 6(a), an initial viewpoint 611 is located at a point 612 on an ultrasound image 610. Although a viewpoint may not be actually displayed on the ultrasound image 610, the viewpoint is displayed as a camera for convenience of explanation.

Referring to FIG. 6(b), it is necessary for a user to see an ultrasound image 620 and move a viewpoint 621 from a point 622 to a fork to a point 622 and a point 623 by using a trackball. Next, referring to FIG. 6(c), it is necessary for the user to see an ultrasound image 630 and move a viewpoint 631 to a point 633. Next, referring to FIG. 6(d), to move to a point 644 on an ultrasound image 640, it is necessary for the user to move a viewpoint 641 to a fork to a point 643 and the point 644. Next, referring to FIG. 6(e), it is necessary for the user to move a viewpoint 651 to a final destination point 654 on an ultrasound image 650. In the related art as described above, it is necessary for a user to manually move an viewpoint by using a trackball, and thus it is not convenient to move a viewpoint for an ultrasound diagnosis.

Furthermore, in FIG. 6, if there are a plurality of branches, it is not easy to distinguish regions already observed by a user from regions not yet observed by the user. For example, the user moved the viewpoint 641 from the point 643 to the branch on the ultrasound image 640. Since a region corresponding to the point 642 is a region already observed by the user on the ultrasound image 610, the user may want to observer a region corresponding to the point 644. However, since a moving path or an observed point is not displayed on the ultrasound image 640 at the ultrasound diagnosis apparatus 300 in the related art, the user may not be sure whether an unobserved point is the point 642 or the point 644. Furthermore, if the ultrasound image 640 is a real-time image, the ultrasound image 640) may be continuously changed, and thus a serious problem may occur. The inventive concept may resolve the problem in the related art.

Operations of an ultrasound diagnosis apparatus according to an embodiment will be described in detail with reference to FIGS. 7 through 17. Furthermore, the ultrasound diagnosis apparatus 300 shown in FIG. 4 will be exemplified below as an ultrasound diagnosis apparatus according to an embodiment.

Figure 7:
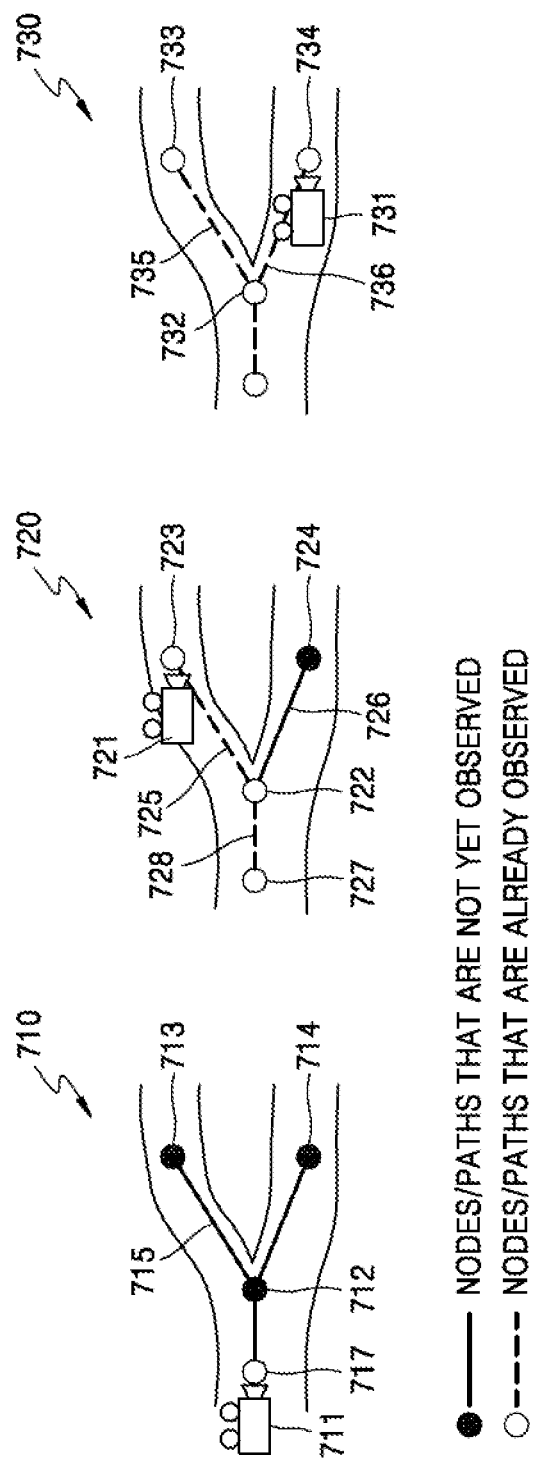
FIG. 7 is a diagram showing movement of a viewpoint on an ultrasound image according to an embodiment.

FIG. 7 is a diagram showing movement of a viewpoint on an ultrasound image according to an embodiment.

Based on at least one of a first ultrasound image 710 and ultrasound data, the control unit 320 may obtain nodes 717, 712, 713, and 714. Furthermore, trunk lines 715, 716, and 718 between the nodes 717, 712, 713, and 714 may be obtained. The nodes 717, 712, 713, and 714 and the trunk lines 715, 716, and 718 may be formed as a tree-like structure. Nodes (the nodes 717, 712, 713, and 714) may be included in first information. The nodes (the nodes 717, 712, 713, and 714) may correspond to a plurality of pixels on the display unit 440, respectively.

The control unit 320 may automatically obtain a sequence of at least two nodes from among nodes and control the image generating unit 310 to move a viewpoint according to the obtained sequence of the nodes and obtain second ultrasound images. For example, the control unit 320 may determine a moving sequence regarding at least one of the nodes 717, 712, 713, and 714 and the trunk lines 715, 716, and 718. To pass every node, the control unit 320 may automatically obtain a sequence of nodes 717->712->713->712->714. Furthermore, the control unit 320 may move a screen image along trunk lines and obtain second ultrasound images. For example, the ultrasound diagnosis apparatus 300, which received a designated input from a user, may move a viewpoint on an ultrasound image 720 and obtain second ultrasound images. In other words, the control unit 320 may move a viewpoint 721 from an initial node 727 to a node 722 via a trunk line 728 on the ultrasound image 720. Next, the control unit 320 may move the viewpoint 721 to a node 723 via a trunk line 725 based on the obtained sequence of the nodes.

Furthermore, the control unit 320 may move a viewpoint based on first information and a received user input and obtain an ultrasound image. For example, referring to the ultrasound image 710, if a viewpoint is located at the node 712, the input unit 430 may receive an input to move the viewpoint to the node 713 from a user. In detail, the user may click the node 713 by using a mouse. The ultrasound diagnosis apparatus 300 may move the viewpoint from the node 712 to the node 713 based on the received input. Furthermore, the ultrasound diagnosis apparatus 300 may obtain an ultrasound image after moving the viewpoint to the node 713.

The display unit 440 may display first information (e.g., nodes and trunk lines) already passed by the viewpoint 721 to be distinguishable from first information (e.g., nodes and trunk lines) not yet passed by the viewpoint 721, on the ultrasound image 720. In other words, the display unit 440 may display nodes and trunk lines, through which the viewpoint 721 passed and ultrasound images are obtained, to be distinguishable from nodes and trunk lines at which ultrasound images are not obtained. In detail, the display unit 440 may display nodes and trunk lines already passed by the viewpoint 721 to be distinguishable from nodes and trunk lines not yet passed by the viewpoint 721 using at least one of different shapes, different colors, and different transparencies, on the ultrasound image 720.

The control unit 320 may display nodes and trunk lines not passed by a viewpoint to be more transparent than nodes and trunk lines passed by the viewpoint. Furthermore, the control unit 320 may display nodes and trunk lines not passed by a viewpoint in colors different from nodes and trunk lines passed by the viewpoint. Furthermore, the control unit 320 may display nodes not passed by a viewpoint as triangles and display nodes passed by the viewpoint as circles. Furthermore, the control unit 320 may display nodes and trunk lines not passed by a viewpoint by using animation effects different from nodes and trunk lines passed by the viewpoint.

Furthermore, the control unit 320 may display a list of nodes and trunk lines. The control unit 320 may display nodes and trunk lines not passed by a viewpoint to be distinguishable from nodes and trunk lines passed by a viewpoint in the list. For example, the ultrasound diagnosis apparatus 300 may display nodes and trunk lines at which second ultrasound images are obtained in bold letters or different fonts from nodes and trunk lines at which no second ultrasound image is obtained. Furthermore, the ultrasound diagnosis apparatus 300 may display designated icons next to letters indicating nodes and trunk lines at which second ultrasound images are obtained.

For example, the nodes 727, 722, and 723 passed by the viewpoint 721 may be displayed as white circles, whereas the node 724 not passed by the viewpoint 721 may be displayed as a black circle. Furthermore, the trunk lines 728 and 725 passed by the viewpoint 721 may be displayed as dotted lines. Therefore, a user may easily recognize nodes and trunk lines that are already observed. FIG. 7 shows an embodiment in which nodes and trunk lines passed by a viewpoint are displayed as dots and lines on the ultrasound image 720. However, the inventive concept is not limited thereto. For example, names of nodes and names of trunk lines passed by a viewpoint may be displayed as a list.

Next, a viewpoint 731 may move from a node 733 to a node 732 via a trunk line 735. Next, the viewpoint 731 may move along a trunk line 736 and arrive at a node 734 according to an obtained sequence of nodes. Since the viewpoint 731 has passed all nodes and trunk lines, the ultrasound diagnosis apparatus 300 may display the nodes and the trunk lines already passed by the viewpoint 731 to be distinguishable from nodes and trunk lines not passed by the viewpoint 731 by using at least one of different shapes, different colors, an different transparencies. Since displaying nodes and trunk lines to be distinguishable from other nodes and trunk lines by using at least one of different shapes, different colors, and different transparencies is already described above, detailed descriptions thereof will be omitted. The input unit 430 may receive an input related to a sequence of at least two nodes from among a plurality of nodes from a user, and the control unit 320 may move a viewpoint based on the received input related to the sequence of the nodes and obtain second ultrasound images.

For example, referring to FIG. 7, the input unit 430 according to an embodiment may receive an input for sequentially selecting the node 713 and the node 714 from a user. For example, the user may recognize that the viewpoint 711 is at the node 717 and may sequentially click the node 713 and the node 714. The control unit 320 may automatically obtain a sequence of nodes 717->712->713->712->714 based on a location of the viewpoint 711 and the received user input. Although the node 712 is not directly selected by the user, the node 712 may be included in the sequence of the nodes to move the viewpoint 711 from the node 717 to the node 713 via trunk lines. The control unit 320 may move a viewpoint according to the obtained sequence of the nodes and obtain second ultrasound image. Since movement of a viewpoint is described above, detailed descriptions\ thereof will be omitted.

Although FIG. 7 shows that a viewpoint moves along trunk lines, the inventive concept is not limited thereto. For example, the input unit 430 may receive an input for sequentially selecting the node 713 and the node 714 from a user. For example, the user may recognize that the viewpoint 711 is at the node 717 and may sequentially click the node 713 and the node 714. The control unit 320 may control the viewpoint to jump from the node 717 to the node 713 and to jump from the node 713 to the node 714 based on the received user input.

Figure 8:
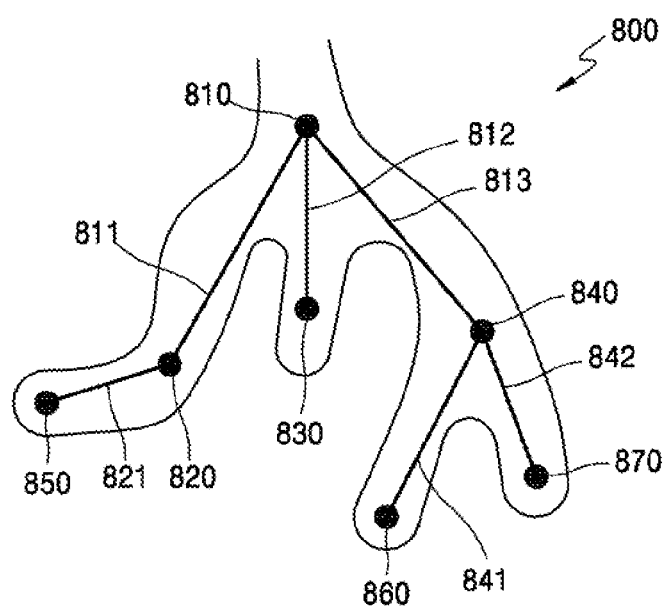
FIG. 8 is a diagram showing movement of a viewpoint on an ultrasound image according to an embodiment.

FIG. 8 is a diagram showing movement of a viewpoint on an ultrasound image according to an embodiment.

Referring to FIG. 8, a target object may be a body part including a tubular tissue, such as a blood vessel, a digestive canal, and a lactiferous drift The image generating unit 310 may obtain a first ultrasound image 800 of the target object based on ultrasound data. The control unit 320 may obtain nodes 810, 820, 830, 840, 850, 860, and 870 and trunk lines 811, 812, 813, 821, 841, and 842 based on at least one of the first ultrasound image 800 and the ultrasound data. The input unit 430 may receive an input from a user, and the control unit 320 may obtain nodes and trunk lines based on the received input. Alternatively, the control unit 320 may extract nodes and trunk lines by performing an image processing to the ultrasound image 800. The image processing may include a centerline extracting algorithm. From among the nodes, the node 850, the node 830, the node 860, and the node 870 are leaf nodes. Furthermore, the node 820 is a path node, and the node 810 and the node 840 are branch nodes.

As described above with reference to FIG. 7, the control unit 320 may move a viewpoint to automatically pass all nodes and trunk lines. However, a user may want to obtain ultrasound images not at all nodes, but at some nodes. The input unit 430 may receive an input for selecting at least one node from among nodes from the user, and the control unit 320 may automatically obtain second ultrasound images based on the selected node(s). Furthermore, the input unit 430 may receive an input for selecting at least one node from among nodes from the user, and the control unit 320 may automatically obtain second ultrasound images based on nodes other than the selected node(s).

In an ultrasound diagnosis apparatus according to an embodiment, the input unit 430 may receive information regarding nodes to pass from a user. For example, the input unit 430 may receive an input for sequentially selecting the node 810, the node 850, and the node 860 from a user. In this case, the control unit 320 may obtain a sequence of moving a viewpoint, such that the viewpoint passes the node 810, the node 850, and the node 860 in the order stated. Furthermore, the ultrasound diagnosis apparatus 300 may include a sequence of moving a viewpoint in first information.

For example, a sequence of moving a viewpoint may be the node 810, the node 820, the node 850, the node 820, the node 810, the node 840, and the node 860. Although the node 820 and node 840 are not nodes received by the input unit 430 from the user, the node 820 and node 840 are nodes on a path for passing nodes received from the user, and thus the control unit 320 may add the node 820 and node 840 to a sequence of moving a viewpoint. The control unit 320 may move a viewpoint along trunk lines according to the sequence of nodes as described above and obtain ultrasound images. In other words, the control unit 320 may move a viewpoint along the trunk line 811, the trunk line 821, the trunk line 821, the trunk line 811, the trunk line 813, and the trunk line 841 and obtain ultrasound images. Although an example in which the input unit 430 receives a selection of nodes from a user is described above, the inventive concept is not limited thereto, and a user may select trunk lines. The input unit 430 may receive a selection of trunk lines and the control unit 320 may move a viewpoint in manners similar to those described above.

In an ultrasound diagnosis apparatus according to another embodiment, a viewpoint may not be moved along trunk lines. For example, the input unit 430 may receive an input for sequentially selecting the node 810, the node 850, and the node 860 from a user. In this case, the control unit 320 may obtain a sequence of moving a viewpoint for passing the node 810, the node 850, and the node 860 in the order stated. For example, the sequence of moving a viewpoint may be the node 810, the node 850, and the node 860. Based on the sequence of nodes as described above, the control unit 320 may obtain an ultrasound image at the node 810, obtain an ultrasound image at the node 850, and finally obtain an ultrasound image at the node 860 in the order stated. Furthermore, a user may select trunk lines instead of nodes. In this case, the control unit 320 may obtain ultrasound images at selected trunk lines.

In an ultrasound diagnosis apparatus according to another embodiment, the input unit 430 may receive information regarding nodes to not to visit from a user. For example, the input unit 430 may receive an input for sequentially selecting the node 820, the node 850, and the node 860 from a user. In this case, the control unit 320 may obtain a sequence of moving a viewpoint to sequentially visit the node 810, the node 830, the node 840, and the node 870 except the node 820, the node 850, and the node 860. For example, the sequence of moving a viewpoint may be the node 810, the node 830, the node 810, the node 840, and the node 870. Although the node 820 and node 840 are not nodes received from the user, the control unit 320 may move a viewpoint along trunk lines based on the sequence of nodes as described above and obtain ultrasound image. In other words, to observe a target object by moving a viewpoint for observing regions corresponding to the node 830, the node 810, the node 840, and the node 870, the control unit 320 may obtain ultrasound images by moving the viewpoint from above to below the trunk line 812, from below to above the trunk line 812, from above to below the trunk line 813, from below and above the trunk line 813, from above to below the trunk line 842, and from below to above the trunk line 842. Although an example in which the input unit 430 receives a selection of nodes to not to visit from a user is described above, the inventive concept is not limited thereto, and a user may select trunk lines to not to visit. The input unit 430 may receive a selection of trunk lines from a user and the control unit 320 may move a viewpoint in manners similar to those described above. In an ultrasound diagnosis apparatus according to another embodiment, a viewpoint may not be moved based on trunk lines.

Figure 9:
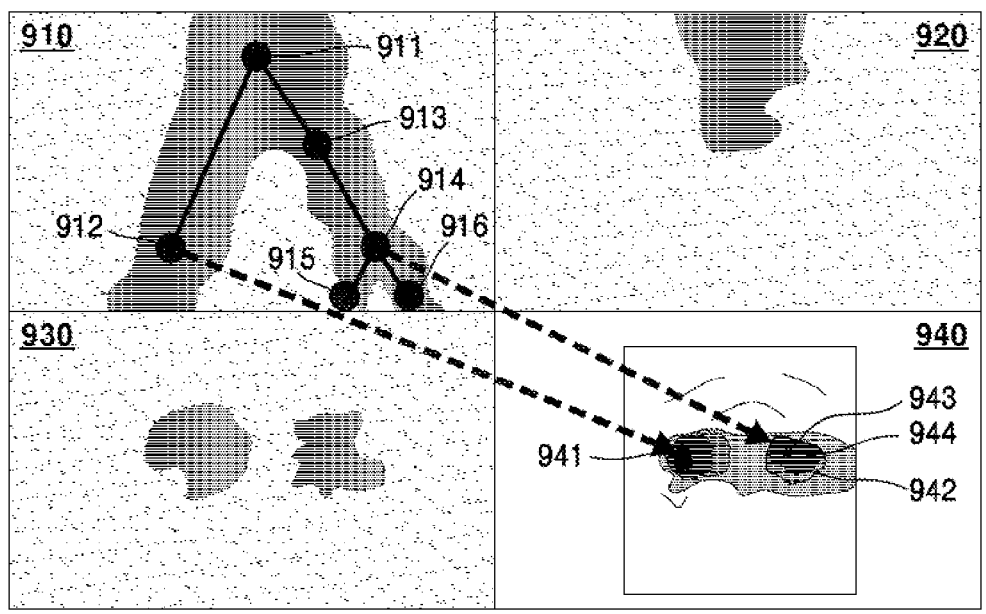
FIG. 9 is a diagram showing an ultrasound image according to an embodiment.

FIG. 9 is a diagram showing an ultrasound image according to an embodiment.

An ultrasound image 910 may be a 2-dimensional (2D) plan view image of a target object. Alternatively, the ultrasound image 910 may be a 3-dimensional (3D) ultrasound image of the target object. An ultrasound image 920 may be a 2D lateral view image or a 2D sectional view image of the target object. An ultrasound image 930 may be a 2D front view image of the target object. For example, an ultrasound image 940 may be a 3D image of the target object viewed from the front based on ultrasound data. The ultrasound diagnosis apparatus 300 may obtain at least one of a plan view image, a lateral view image, a front view image, and a 3D ultrasound image of the target object.

Both a first ultrasound image, which is obtained to determine a region to be observed by a user, and a second ultrasound image, which is an image of a region to be observed by a user, may be displayed in an ultrasound image 900. For example, nodes and trunk lines are displayed on the ultrasound image 910. Since a user may determine a region to observe by selecting nodes and trunk lines on the ultrasound image 910, the ultrasound image 910 may become a first ultrasound image. Furthermore, if the user selects the nodes and trunk lines on the ultrasound image 910, the ultrasound image 910 may be magnified around the corresponding nodes and trunk lines, and the magnified ultrasound image 910 may become a second ultrasound image. Alternatively, a 3D ultrasound image 940 of the target object at the corresponding nodes and trunk lines may become a second ultrasound image. Since the ultrasound image 910 includes the clearest representation of the branched structure of the target object, the above description is given based on the ultrasound image 910. However, the inventive concept is not limited thereto, and a first ultrasound image and a second ultrasound image may be displayed with respect to at least one of the ultrasound image 920, the ultrasound image 930, and the ultrasound image 940.

Nodes 911, 912, 913, 914, 915, and 916 on the ultrasound image 910 may be obtained based on an input from a user received by the input unit 430. Furthermore, the nodes 911, 912, 913, 914, 915, and 916 may also be automatically obtained by the control unit 320. A trunk line may be arranged between a node and another node. The node 912 may correspond to a point 941 on the ultrasound image 940. Furthermore, the node 914 may correspond to a point 942 on the ultrasound image 940. Although relationships of correspondences are indicated with arrows in FIG. 9, no arrow may be displayed on the actual ultrasound image 900. Furthermore, the nodes 915 and 916 may corresponding to points 943 and 944 on the ultrasound image 940, respectively.

Figure 10:
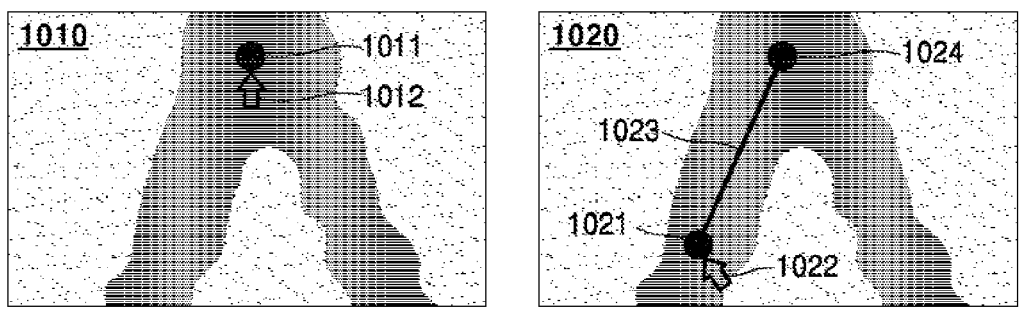
FIG. 10 is a diagram showing a process for obtaining nodes based on a user input, according to an embodiment.

FIG. 10 is a diagram showing a process for obtaining nodes based on a user input, according to an embodiment.

The input unit 430 may receive at least one of inputs for adding, moving, and deleting nodes and trunk lines from a user, and the control unit 320 may modify the nodes and trunk lines.

For example, an ultrasound image 1010 may be a plan view image of a target object. The input unit 430 may receive an input from a user, and the control unit 320 may obtain nodes based on the received input. For example, a user may locate an indicator 1012 at a location for generating a node on the ultrasound image 1010. The input unit 430 may receive an input from the user at location of a node 1011. The control unit 320 may obtain the node 1011 based on the received input. Furthermore, the user may move an indicator 1022 on an ultrasound image 1020. The input unit 430 may receive an input from the user at location of a node 1021. The control unit 320 may obtain the node 1021 based on the received input. Furthermore, the control unit 320 may automatically obtain a trunk line 1023 based on a node 1024 and the node 1021.

Furthermore, as described above, the control unit 320 may obtain the node 1021 based on the received input and determine a sequence of moving a viewpoint with respect to the node 1024 and the node 1021. For example, since the node 1021 is additionally obtained after the node 1024, the control unit 320 may obtain a sequence of moving a viewpoint with respect to nodes, such that the viewpoint sequentially passes the node 1024 and the node 1021. The control unit 320 may move a viewpoint based on the sequence of nodes and first information and obtain ultrasound images.

Figure 11A:
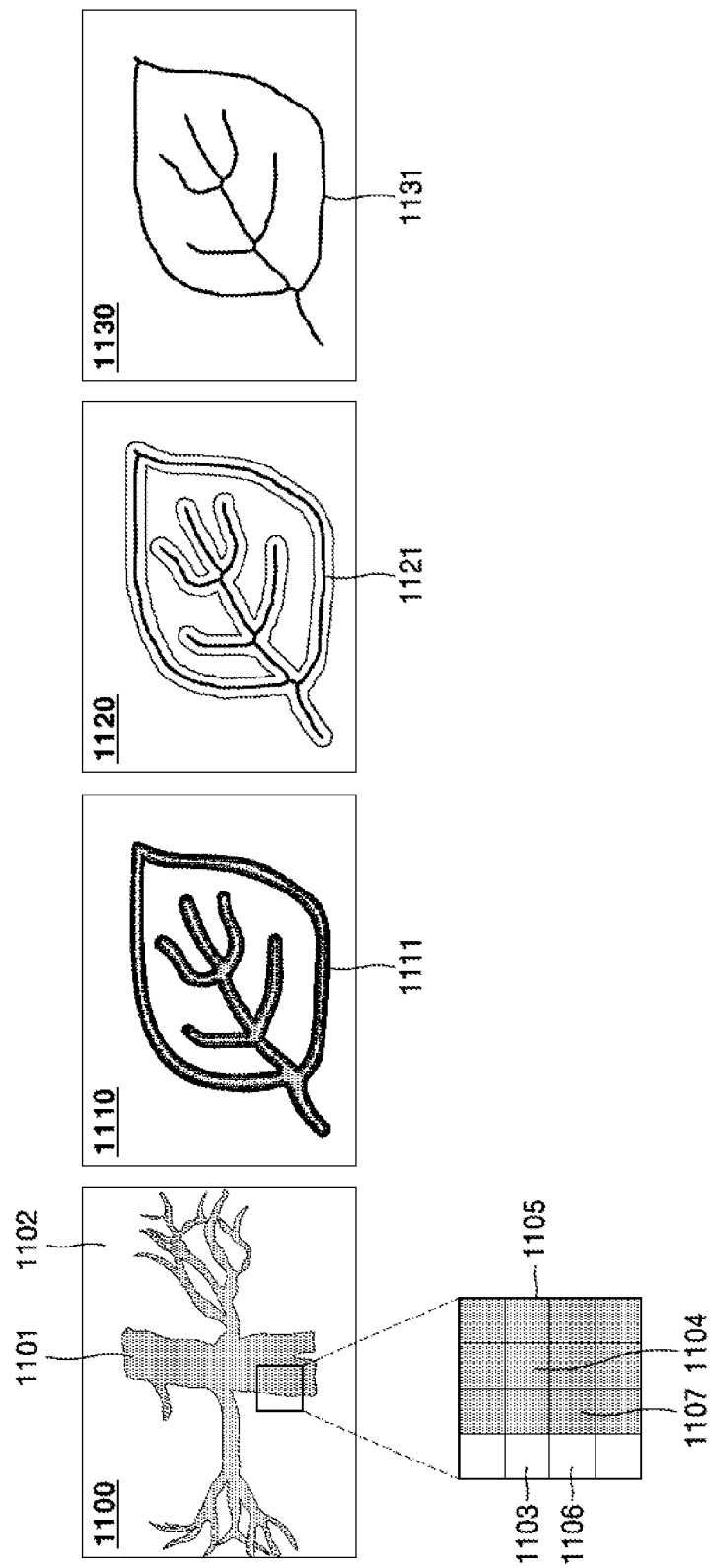
FIGS. 11A through 11C are diagrams showing that a control unit automatically obtains nodes and trunk lines, according to an embodiment.
Figure 11B:
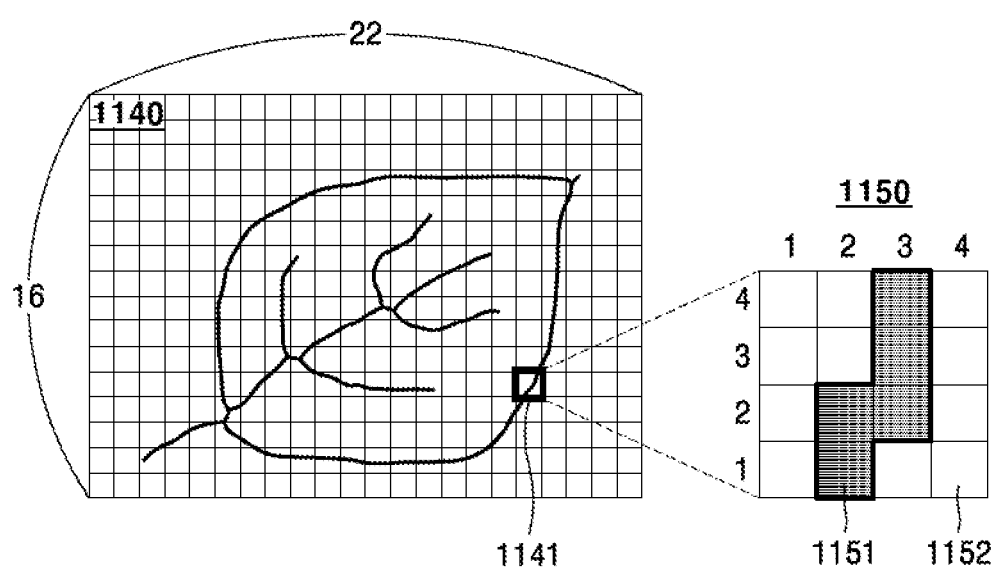
Figure 11C:
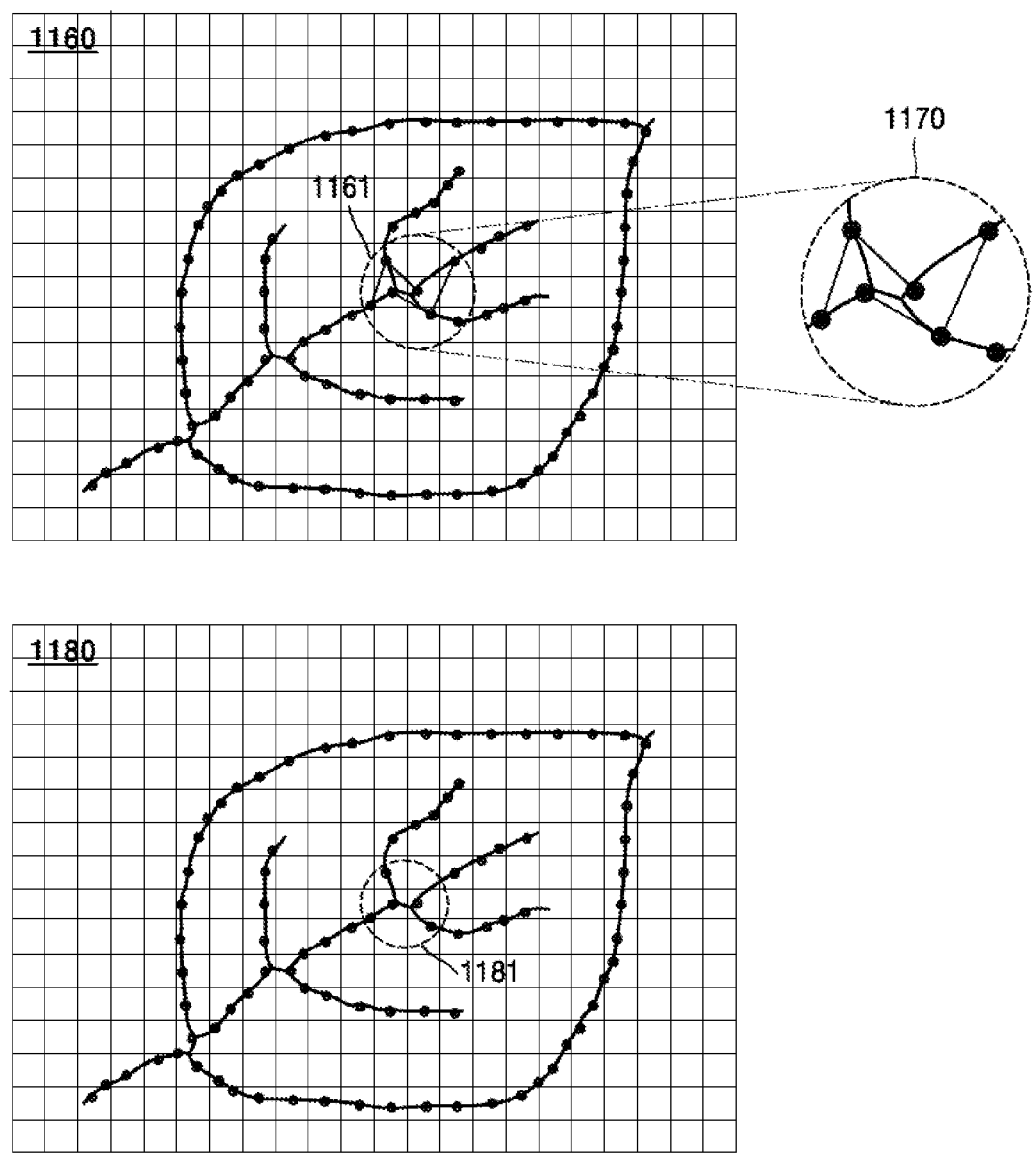

FIGS. 11A through 11C are diagrams showing that a control unit automatically obtains nodes and trunk lines, according to an embodiment.

The control unit 320 may extract nodes and trunk lines from at least one of ultrasound data and an ultrasound image by using a centerline extracting algorithm. An ultrasound image 1100 is an image showing an ultrasound image of a blood vessel, which is a target object. A blood vessel has a 3D structure and is complicatedly tangled. The ultrasound diagnosis apparatus 300 may obtain nodes and trunk lines by performing an image processing to an image of a 3D structure. However, for convenience of explanation, a process of obtaining nodes and trunk lines will be described below in relation to a case in which a target object has a 2D leaf-like shape.

The control unit 320 may perform an image processing, such that a structure extracted from the ultrasound image 1100 (e.g., a blood vessel) is clearly distinguishable from a structure that is not extracted. For example, referring to FIG. 11A, in the ultrasound image 1100, a background 1102 may be displayed in white, whereas a target object 1101 may be displayed in black. The ultrasound diagnosis apparatus 300 may obtain a centerline of a target object 1111 by performing an image processing with respect to the ultrasound image 1100. For example, the control unit 320 may calculate distances between the respective pixels included in the black area of the target object 1101 to the white area of the background 1102. For example, referring to a magnified image 1105 of the ultrasound image 1100, the control unit 320 may determine the closest white pixel 1103 of the background 1102 to a black pixel 1104 included in the target object 1101. Furthermore, the control unit 320 may calculate a distance between the black pixel 1104 and the determined white pixel 1103, wherein the distance is '2.' Furthermore, the control unit 320 may determine the closest white pixel 1106 of the background 1102 to a black pixel 1107 included in the target object 1101. Furthermore, the control unit 320 may calculate a distance between the black pixel 1107 and the determined white pixel 1106, wherein the distance is '1.' Furthermore, the control unit 320 may obtain an image 1110 including the calculated distances as pixels (1107,1104) values.

Referring to the image 1110, a target object 1111 to which calculated pixel values are applied is shown. In other words, brighter colors may be displayed toward the centerline of the target object 1111, and darker colors may be displayed toward the background.

The control unit 320 may apply a suitable kernel to the image 1110. For example, a suitable kernel may be a Laplace-Gaussian kernel having a radius of 2. The control unit 320 may obtained an image-processed image 1120. The image 1120 may obtain a centerline 1121 based on the image 1110.

The control unit 320 may obtain only a centerline 1131 by performing an image processing with respect to the image 1120. An image 1130 may include a the black centerline 1131 and the white background.

Furthermore, referring to FIG. 11B, the control unit 320 may partition the image 1130. Partitioning refers to splitting the image 1130 and analyzing split pieces of the image 1130. Referring to an image 1104, the image 1130 is split into 16×22 pieces. Referring to an image 1150, which is a magnified image of a piece 1141, the piece 1141 consists of 4×4 pixels. The image 1150 may include black pixels 1151 and white pixels 1152. The control unit 320 may determine the center pixel of black pixels of the piece 1141 for each of the pieces of the image 1140. For example, coordinates of the black pixels in the image 1105 may be (2, 1), (2, 2), (3, 2), (3, 3), and (3, 4), respectively. Coordinate of the center pixel may be calculated as shown in Equation 1 below.

$$XCM = (\Sigma i \in \text{black pixels } Xi)/\text{number of black pixels}$$

$$YCM = (\Sigma i \in \text{black pixels } Yi)/\text{number of black pixels} \quad \text{<Equation 1>}$$

In other words, XCM may be (2+2+3+3+3)/5=2.6 and YCM may be (1+2+2+3+4)/5=2.4, where (XCM, YCM) may be (3, 2) by rounding up the respective values. Calculated center pixels may become nodes. Furthermore, a line interconnecting a node and another node may become a trunk line.

Referring to FIG. 11C, as described above, the control unit 320 may obtain an image 1160 consisting of center pixels and lines interconnecting the center pixels. However, a region 1161 of the image 1160 may include small cycles 1170. The control unit 320 may obtain an image 1180 by removing such cycles from the image 1160. Referring to FIG. 11C, there is a difference between a region 1181 and the region 1161. The control unit 320 may obtain second ultrasound images based on nodes and trunk lines obtained as described above with reference to FIGS. 11A through 11C.

Figure 12:
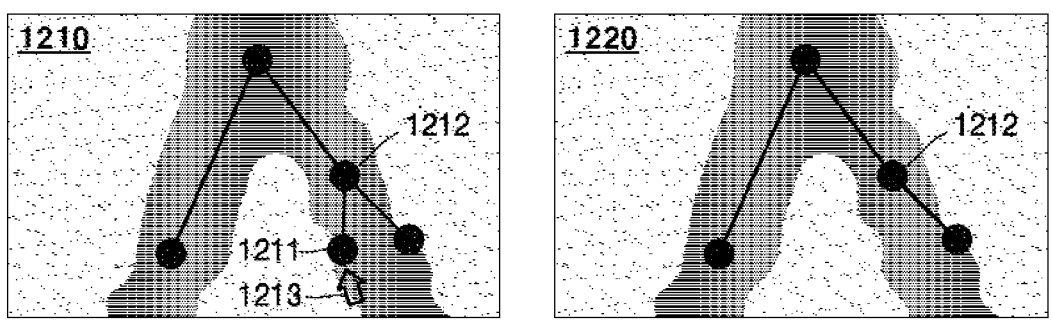
FIG. 12 is a diagram showing a process of modifying nodes according to an embodiment.

FIG. 12 is a diagram showing a process of modifying nodes according to an embodiment.

An ultrasound image 1210 may include nodes. A user may select a node 1211 by moving an indicator 1213 to delete a node. The input unit 430 may receive an input from the user. The control unit 320 may delete the node 1211 based on the received input. Referring to an ultrasound image 1220, the node 1211 is deleted. Furthermore, a trunk line interconnecting the node 1211 and a node 1212 may also be deleted. Although FIG. 12 shows an embodiment for deleting a node, location of a node may be modified or a node may be added in similar manners.

Figures 13A, 13B:
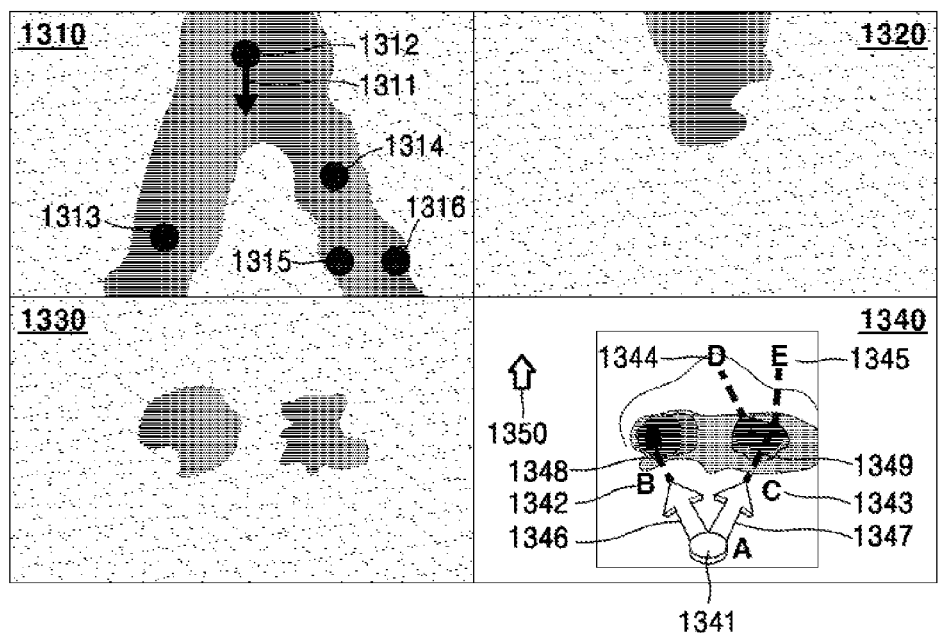
FIG. 13A is a diagram showing movement between nodes, according to an embodiment.
FIG. 13B is a diagram showing a node list according to an embodiment.

FIG. 13A is a diagram showing movement between nodes, according to an embodiment.

An ultrasound image 1310 may be a 2D plan view image of a target object. An ultrasound image 1320 may be a 2D lateral view image of the target object. An ultrasound image 1330 may be a front view image of the target object. An ultrasound image 1340 may be a 2D image of the target object based on ultrasound data. The ultrasound diagnosis apparatus 300 may obtain at least one of a plan view image, a lateral view image, a front view image, and a 3D ultrasound image of a target object.

In an ultrasound image 1300, a first ultrasound image used by a user for determining a region to observe and a second ultrasound image, which is an image of a region to observe used by a user to observe an ultrasound image of target object, may be displayed together. For example, an ultrasound image 1310 may be an ultrasound image obtained by an ultrasound diagnosis apparatus for a user to observe a target object and an ultrasound image used by the user to determine a region to observe.

In detail, nodes may be displayed on the ultrasound image 1310 without a trunk line. The ultrasound diagnosis apparatus 300 may obtain trunk lines based on an input from a user and display the trunk lines. Since the user may determine a region to observe by selecting nodes on the ultrasound image 1310, the ultrasound image 1 image generating unit 310 may be a first ultrasound image. Furthermore, if the user selects nodes on the ultrasound image 1310, the ultrasound image 1310 may be magnified based on the selected nodes, and the magnified ultrasound image 1310 may become a second ultrasound image. Furthermore, the 3D ultrasound image 1340 of the target object obtained by using a selected node as a viewpoint may become a second ultrasound image. Since the ultrasound image 1310 includes the clearest representation of the branched structure of the target object, the above description is given based on the ultrasound image 1310. However, the inventive concept is not limited thereto, and a first ultrasound image and a second ultrasound image may be displayed with respect to at least one of the ultrasound image 1320, the ultrasound image 1330, and the ultrasound image 1340.

The control unit 320 may obtain second information indicating at least one of location and direction of a viewpoint based on first information. Furthermore, the display unit 440 may display an image, in which at least one of the first information and the second information is displayed on a first ultrasound image. Here, a direction of a viewpoint refers to a direction at a designated location for obtaining an ultrasound image. For example, second information, that is, location of a viewpoint and a line of sight 1311 may be displayed on the ultrasound image 1310. The location of the viewpoint may become a node 1312. Based on the location of the viewpoint and the line of sight 1311, a 3D ultrasound image of the target object may be displayed in the ultrasound image 1340. The ultrasound diagnosis apparatus 300 may receive an input for modifying a line of sight, and at least one of the ultrasound images 1310 through 1340 may be modified based on the modified line of sight.

A current viewpoint may be located at the node 1312. In the ultrasound image 1340, names may be allocated to the respective nodes. For example, the node 1312, the node 1313, the node 1314, the node 1315, and the node 1316 may be named as an Anode 1341, a Bnode 1342, a Cnode 1343, a Dnode 1344, and an Enode 1345, respectively. Furthermore, the ultrasound image 1340, in which nodes with allocated names are displayed, may be displayed at the display unit 440.

Furthermore, in the ultrasound image 1340, icons 1346 and 1347 for moving a viewpoint may be displayed. The ultrasound diagnosis apparatus 300 may select an icon based on an input from a user and move a viewpoint. For example, a user may select the icon 1347 by moving an indicator 1350 by using the input unit 430. The control unit 320 may move a viewpoint from the Anode 1341 to the Cnode 1343 via a trunk line 1349 based on the selection received from the user. Furthermore, the user may select the icon 1346 by moving the indicator 1350 by using the input unit 430. The control unit 320 may move a viewpoint from the Anode 1341 to the Bnode 1342 via a trunk line 1348 based on the selection received from the user.

FIG. 13B is a diagram showing a node list according to an embodiment.

According to an embodiment, a node list 1360 may be displayed at a designated region of the display unit 440 together with the ultrasound image 1300. In the node list 1360, nodes 1361 through 1365 obtained by the control unit 320 may be displayed. Furthermore, a user may move a viewpoint by selecting one of nodes by using the indicator 1350. For example, the user may select the Bnode 1362 by moving the indicator 1350 by using the input unit 430. The control unit 320 may move a viewpoint from the Anode 1341 to the Bnode 1342 based on the selection received from the user.

Furthermore, in the node list 1360, a node at which a second ultrasound image is obtained (that is, a node passed by a viewpoint) may be displayed different from a node at which no second ultrasound image is obtained (that is, a node not passed by the viewpoint). In the node list 1360, nodes at which second ultrasound images are obtained may be displayed in a different text format from nodes at which no second ultrasound image is obtained. For example, the ultrasound diagnosis apparatus 300 may display texts corresponding to nodes at which second ultrasound images are obtained in bold or in a font different from nodes at which no second ultrasound image is obtained. Furthermore, designated icons may be displayed next to texts corresponding to nodes at which second ultrasound images are obtained.

Although FIG. 13B only shows a node list, a trunk line list regarding trunk lines may also be displayed. Furthermore, in a trunk line list, trunk lines at which second ultrasound images are obtained (that is, trunk lines passed by a viewpoint) may be displayed differently from trunk lines at which no second ultrasound image is obtained (that is, trunk lines not passed by the viewpoint).

FIGS. 14 through 17 are diagrams showing movement between nodes, according to an embodiment.

Figure 14:
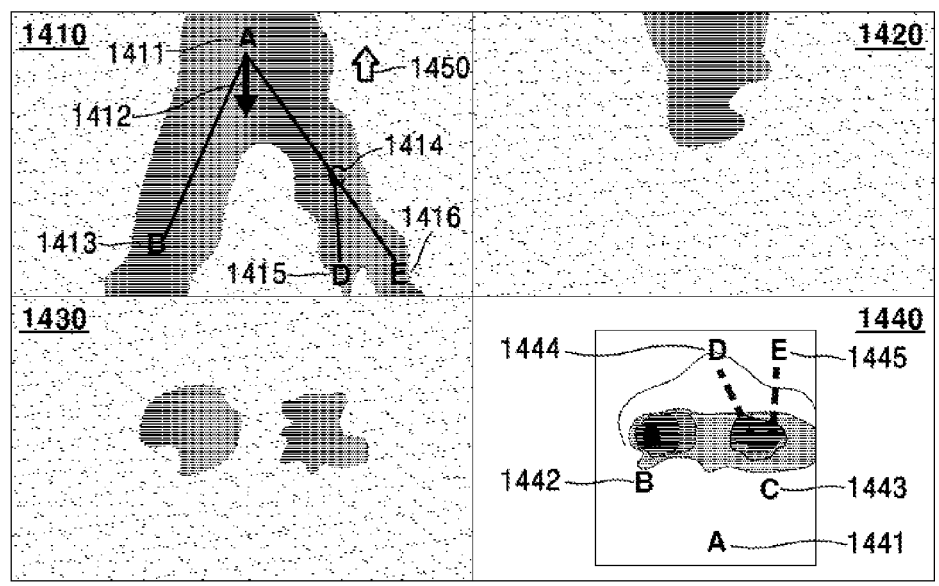
FIG. 14 is a diagram showing ultrasound images according to an embodiment.

FIG. 14 is a diagram showing ultrasound images according to an embodiment.

An ultrasound image 1410 may be a 2D plan view image of a target object. An ultrasound image 1420 may be a 2D lateral view image of the target object. An ultrasound image 1430 may be a front view image of the target object. An ultrasound image 1440 may be a 2D image of the target object based on ultrasound data. The ultrasound diagnosis apparatus 300 may obtain at least one of a plan view image, a lateral view image, a front view image, and a 3D ultrasound image of a target object.

Referring to FIG. 14, in the ultrasound image 1410, nodes 1411, 1413, 1414, 1415, and 1416 may be displayed. Furthermore, trunk line interconnecting a node and another node may be displayed. Furthermore, in the 3D ultrasound image 1440 corresponding to the ultrasound image 1410, nodes 1441, 1442, 1443, 1444, and 1445 may be displayed. In the ultrasound image 1410, a line of sight 1412 may be displayed. Based on the line of sight 1412, the 2D lateral view ultrasound image 1420, the 2D front view ultrasound image 1430, and the 3D image 1440 of the target object may be displayed. The ultrasound diagnosis apparatus 300 may receive an input for modifying a line of sight from a user, and the ultrasound images 1410 through 1440 may be modified based on the modified line of sight.

The user may move a viewpoint to a node in the ultrasound image 1410 or the ultrasound image 1440 by selecting the corresponding node by using an indicator 1450. Furthermore, as described above with reference to FIG. 8, a plurality of nodes to visit or a plurality of node to not to visit may be selected. For example, the user may select the nodeC 1414 or the node 1443 by using the indicator 1450 via the input unit 430. The control unit 320 may control the ultrasound diagnosis apparatus 300 to move a viewpoint from the nodeA 1411 to the nodeC 1414 based on location of the viewpoint and selection of the user and obtain second ultrasound images.

Figure 15A:
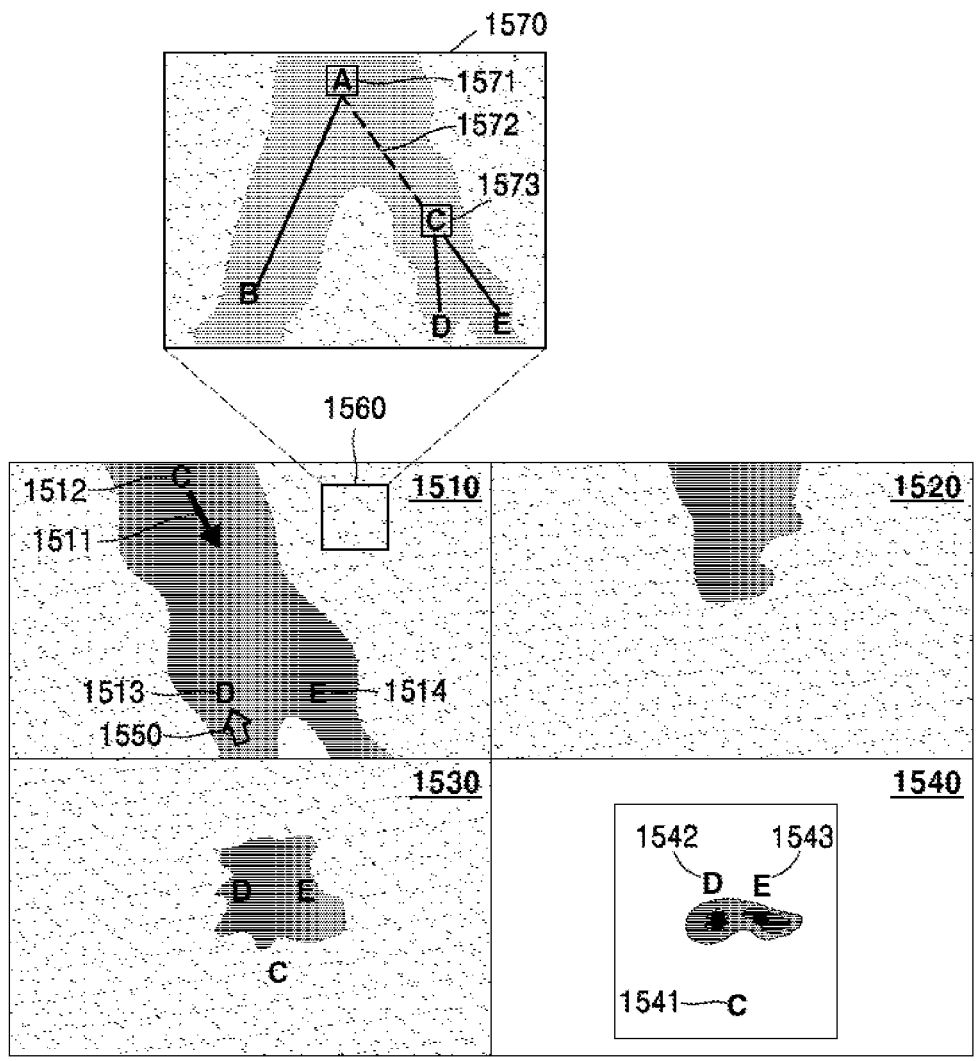
FIGS. 15A and 15B are diagrams showing an ultrasound image according to an embodiment.
Figure 15B:
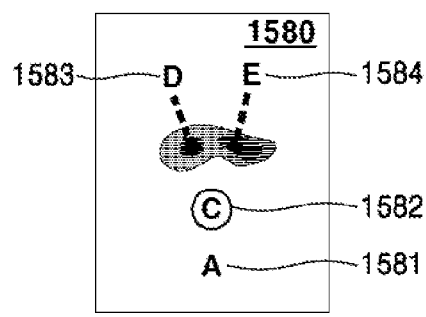

FIGS. 15A and 15B are diagrams showing an ultrasound image according to an embodiment.

Referring to FIG. 15A, it is clear that a viewpoint is moved to a nodeC 1512 or 1541 as the user selected a node C in FIG. 14. Ultrasound images 1510, 1520, 1530, and 1540 are ultrasound images in a case where a viewpoint is at the nodeC. The ultrasound image 1510 may be a 2D plan view image of a target object. The ultrasound image 1520 may be a 2D lateral view image of the target object. The ultrasound image 1530 may be a front view image of the target object. The ultrasound image 1540 may be a 2D image of the target object based on ultrasound data. The ultrasound image 1510 may be a magnified image of the ultrasound image 1410 of FIG. 14. The ultrasound image 1520, the ultrasound image 1530, and the ultrasound image 1540 may be ultrasound image obtained based on a line of sight 1511.

Referring to FIG. 15A, mini ultrasound images 1570 may be displayed at designated regions in ultrasound images. For example, the mini ultrasound image 1570 may be displayed at a designated region 1560 of the ultrasound image 1510. A mini ultrasound image may be a first ultrasound image used by a user to determine a region to observe.

In the mini ultrasound image 1570, all of nodeA through nodeE may be displayed, unlike in the ultrasound image 1510. Nodes and trunk lines at which second ultrasound images are obtained by the ultrasound diagnosis apparatus 300 may be displayed in the mini ultrasound image 1570 differently from nodes and trunk lines at which no second ultrasound image is obtained. Therefore, a user may easily recognize nodes and trunk lines at which second ultrasound images are obtained. For example, since the nodeA 1571 and the nodeC 1573 are nodes observed by a user, names of the nodes (that is, A and C) may be displayed with rectangular borders. Alternatively, A and C, which are names of nodes, may be displayed in bold. Furthermore, since the trunk line 1571 is a trunk line that is already observed, the trunk line 1571 may be displayed as a dotted line, unlike the other trunk lines. A user may move a viewpoint to a node by clicking the corresponding node on the mini ultrasound image 1570. As described above with reference to FIG. 8, a plurality of nodes to visit or a plurality of node to not to visit may be selected.

Furthermore, the ultrasound image 1510 may include nodes 1512, 1513, and 1514. Furthermore, there may be trunk lines interconnecting nodes and nodes. In the ultrasound image 1510, a line of sight icon 1511 may be displayed. A user may modify the line of sight icon 1511 by using the input unit 430. Furthermore, the 3D ultrasound image 1540 corresponding to the ultrasound image 1510 may include the nodes 1541, 1542, and 1543. In the ultrasound image 1540, a line of sight icon (not shown) may be displayed. A user may modify a line of sight by modifying the line of sight icon by using the input unit 430. Based on the modified line of sight, the ultrasound images 1510 through 1540 may be modified.

A user may move a viewpoint to one of nodes in the ultrasound image 1510 or the ultrasound image 1540 by selecting the corresponding node by using an indicator 1550. Furthermore, as described above with reference to FIG. 8, a plurality of nodes to visit or a plurality of node to not to visit may be selected. For example, a user may select the nodeD 1513 or 1542 by using the indicator 1550 via the input unit 430. The control unit 320 may control an ultrasound diagnosis apparatus to move a viewpoint from the nodeC 1512 to the nodeD 1513 based on a selection of the user and obtain ultrasound images.

Furthermore, referring to FIG. 15B, the display unit 440 may display a 3D ultrasound image 1580 only. In the 3D ultrasound image 1580, a nodeA 1581, a nodeC 1582, a nodeD 1583, and a nodeE 1584 may be displayed. The display unit 440 may display the nodeC 1582 by using at least one of a shape, a symbol, an image, and a text different from the other nodes 1581, 1583, and 1584 to indicate a node at which a current viewpoint is located. For example, the nodeC 1583 may be displayed with a circular border. Furthermore, the nodeC 1582 may be displayed in bold text.

Figure 16:
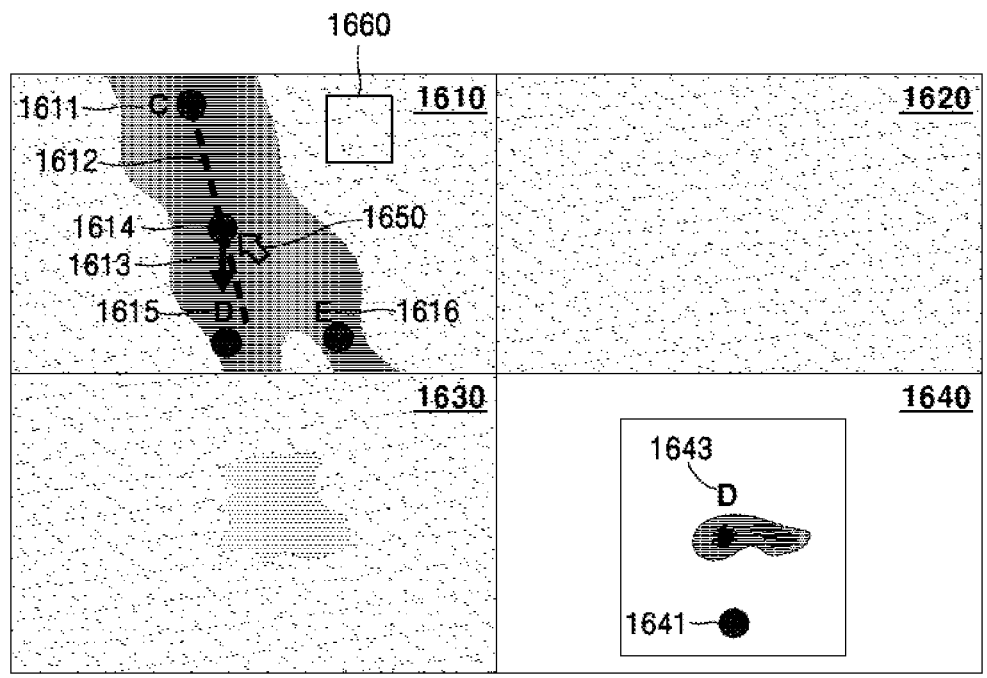
FIG. 16 is a diagram showing an ultrasound image according to an embodiment, continued from FIG. 14.

The ultrasound diagnosis apparatus 300 may receive an input from a user by using the input unit 430. Furthermore, the ultrasound diagnosis apparatus 300 may receive an input selecting at least one of nodes 1581, 1583, and 1584 from the user. The ultrasound diagnosis apparatus 300 may move a viewpoint based on the selection of the user and obtain ultrasound images. For example, a user may move the indicator 1550 by using a mouse. Furthermore, the user may select the nodeD 1583 by moving the indicator 1550. The ultrasound diagnosis apparatus 300 may obtain an ultrasound image by moving a viewpoint from the nodeC\ 1582 to the nodeD 1583. The obtained ultrasound image may be a 2D or 3D ultrasound image. The user may observe the 3D ultrasound image 1580 via a large-size display device and perform an endoscopic diagnosis with respect to a target object. FIG. 16 is a diagram showing an ultrasound image according to an embodiment, continued from FIG. 14.

Referring to FIG. 16, a viewpoint 1614 is located on a trunk line between a nodeC 1611 and a nodeD 1615. An ultrasound diagnosis apparatus may obtain ultrasound images 1610, 1620, 1630, and 1640 not only on nodes, but also on trunk lines. A line of sight 1613 on a trunk line may face toward the nodeD 1615. However, the inventive concept is not limited thereto. Nodes 1611, 1615, and 1616 may be displayed in the ultrasound image 1610. In the 1610, the viewpoint 1614 may be displayed. Furthermore, in the ultrasound image 1640, a viewpoint 1641 and a line of sight icon (not shown) may be displayed. The viewpoint 1641 of the ultrasound image 1640 may correspond to the viewpoint 1614 of the ultrasound image 1610. Furthermore, the nodeD 1643 may be displayed in the ultrasound image 1640. As described above with reference to FIGS. 14 and 15, a user may select a node on an ultrasound image by using the indicator 1550 via the input unit 430, and the control unit 320 may move a viewpoint to the corresponding node based on the selection of the user.

Furthermore, mini ultrasound images 1660 may be displayed at designated regions in ultrasound images. For example, the mini ultrasound image 1660 may be displayed at a designated region of the ultrasound image 1610. The mini ultrasound image 1660 may be a first ultrasound image used by a user to determine a region to observe.

The input unit 430 may receive an input related to a speed of moving a viewpoint between a node and another node from a user, and the control unit 320 may move a viewpoint on a screen image based on the speed of movement and obtain ultrasound images. Furthermore, the input related to a speed of moving a viewpoint may include moving time between nodes.

In other words, a user may select a speed of moving a viewpoint between nodes. For example, the control unit 320 may move a viewpoint from the nodeC 1611 to the nodeD 1615 based on a speed selected by the user. Therefore, the user may easily observe ultrasound images 1610, 1620, 1630, and 1640 even between the nodeC 1611 and the nodeD 1615. For example, the user may set a speed of moving a viewpoint between nodes, thereby moving a viewpoint slowly at regions to be observed in detail.

Figure 17:
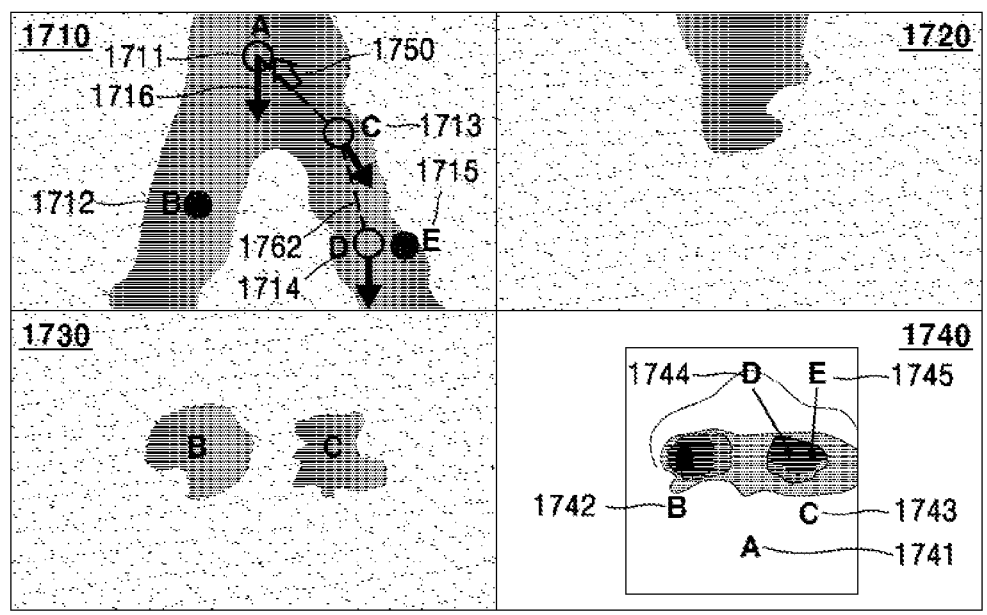
FIG. 17 is a diagram showing an ultrasound image according to an embodiment; and, FIG. 18 is a diagram showing that ultrasound data indicated in a coordinate system, according to an embodiment.

FIG. 17 is a diagram showing an ultrasound image according to an embodiment.

An ultrasound image 1 first ultrasound image 710 includes a path for moving a viewpoint. As described above with reference to FIGS. 14 through 16, a viewpoint passed a nodeA 1711, a trunk line 1761, a nodeC 1713, a trunk line 1762, and a nodeD 1714 in the order stated. The control unit 320 may display nodes at which second ultrasound images are obtained as passed by the viewpoint differently from nodes at which no second ultrasound image is obtained. Furthermore, the control unit 320 may display trunk lines at which second ultrasound images are obtained as passed by the viewpoint differently from trunk lines at which no second ultrasound image is obtained. For example, the nodeA 1711, the nodeC 1713, and the nodeD 1714 may be displayed together with lines of sight 1717 and 1718. Furthermore, the trunk line 1761 and the trunk line 1762 may be displayed as dotted lines. Therefore, a user may easily recognize regions that are already observed. In FIG. 17, the ultrasound image 1710 may be always displayed at a designated region of a display unit as a mini ultrasound image, and the user may easily recognize regions that are already observed. Since detailed descriptions of a mini ultrasound image is given above with reference to FIG. 15A, detailed descriptions thereof will be omitted.

Referring to an ultrasound image 1740, since the nodeA 1741, the nodeC 1743, and the nodeD 1744 are regions that are already observed, the nodeA 1741, the nodeC 1743, and the nodeD 1744 may be displayed differently from other nodes. For example, the nodeA 1741, the nodeC 1743, and the nodeD 1744 may be displayed with bold texts. However, the inventive concept is not limited thereto. A viewpoint arrived at the nodeA 1741 again, and a user may easily recognize that the nodeA 1741, the nodeC 1743, and the nodeD 1744 are regions that are already observed.

The ultrasound diagnosis apparatus 300 according to an embodiment may include an ultrasound data obtaining unit, the input unit 430, and the control unit 320. The ultrasound data obtaining unit may obtain ultrasound data by scanning a target object. Furthermore, the input unit 430 may receive an input from a user. Furthermore, the control unit 320 may obtain first information including a plurality of nodes based on ultrasound data, may move a viewpoint based on the first information and the received input, and obtain ultrasound images. For example, the user may select a node by using the input unit 430 including a mouse or a keyboard. The control unit 320 may obtain an ultrasound image, which is viewed from the node selected by the user, based on the ultrasound data.

The ultrasound diagnosis apparatus 300 according to an embodiment may include an ultrasound data obtaining unit, the input unit 430, and the control unit 320. The ultrasound data obtaining unit may obtain ultrasound data by scanning a target object. Furthermore, the control unit 320 may obtain first information including at least one of a plurality of nodes and a plurality of trunk lines. Furthermore, the control unit 320 may move a viewpoint based on the first information. Furthermore, the display unit 440 may display first information passed by the viewpoint to be distinguishable from first information not passed by the viewpoint. For example, as described above, the control unit 320 may move a viewpoint based on a selection of a user. The display unit 440 may display first information passed by the viewpoint to be distinguishable from first information not passed by the viewpoint. In other words, the first information passed by the viewpoint may be displayed by using at least one of a transparency, a color, and a shape different from the first information not passed by the viewpoint.

The ultrasound diagnosis apparatus 300 according to an embodiment may include the image generating unit 310, the input unit 430, and the control unit 320. The image generating unit 310 may obtain a first ultrasound image by scanning a target object. The input unit 430 may receive an input from a user. Furthermore, the control unit 320 may obtain first information including a plurality of nodes included in the first ultrasound image based on the received input. Furthermore, the control unit 320 may obtain a sequence of nodes based on the received input. Furthermore, the control unit 320 may move a viewpoint based on the sequence of nodes and the first information and obtain second ultrasound images. For example, the ultrasound diagnosis apparatus 300 may simultaneously obtain first information and a sequence of moving a viewpoint based on a user input. Furthermore, based on the sequence of moving a viewpoint, the ultrasound diagnosis apparatus 300 may sequentially move the viewpoint and obtain second ultrasound images.

An ultrasound diagnosis apparatus may provide a user interface enabling a user to easily move a viewpoint.

It should be understood that the exemplary embodiments described therein should be considered in a descriptive sense only and not for purposes of limitation. Descriptions of features or aspects within each embodiment should typically be considered as available for other similar features or aspects in other embodiments.

While one or more exemplary embodiments have been described with reference to the figures, it will be understood by those of ordinary skill in the art that various changes in form and details may be made therein without departing from the spirit and scope of the inventive concept as defined by the following claims.

What is claimed is:

1. An ultrasound diagnosis apparatus comprising:
at least one processor configured to implement:
an image generation unit configured to generate a first ultrasound image based on ultrasound data obtained by scanning a target object including a tubular object; and
a control unit configured to obtain first information of a plurality of nodes indicating nodal points included in the at least one of plurality of lines through the tubular object, based on the first ultrasound image, determine a node among the plurality of nodes as a viewpoint, and to control the image generator to generate a second ultrasound image based on the ultrasound data and the determined viewpoint,
wherein the control unit is further configured to:
automatically obtain a sequence of nodes regarding at least two of the nodes,
determine the viewpoint according to the obtained sequence of nodes, and
control a display to display the first ultrasound image including the plurality of nodes and the second ultrasound image,
wherein one or more nodes from among the plurality of nodes, at which the second ultrasound image is obtained, is displayed differently from one or more nodes from among the plurality of nodes, at which the second ultrasound image is not obtained, in the first ultrasound image.

2. The ultrasound diagnosis apparatus of claim 1, wherein the control unit obtains second information including at least one of location and direction of the viewpoint based on the first information,
further comprising a display unit, which displays an image in which at least one of the first information and the second information is displayed on the first ultrasound image.

3. The ultrasound diagnosis apparatus of claim 1, wherein the control unit obtains trunk lines interconnecting the nodes and the other nodes,
based on the plurality of nodes and trunk lines, the control unit obtains a structure included in the first ultrasound image, and
the first information comprises at least one of the trunk lines and the structure.

4. The ultrasound diagnosis apparatus of claim 3, wherein the structure is a graph having a tree structure.

5. The ultrasound diagnosis apparatus of claim 1, further comprising an input unit configured to receive an input related to first information from a user via a particular location of the first ultrasound image.

6. The ultrasound diagnosis apparatus of claim 5, wherein the control unit is further configured to perform at least one of operations for adding, moving, and deleting at least one of the nodes and trunk lines based on the received input.

7. The ultrasound diagnosis apparatus of claim 5, wherein the input unit receives an input for selecting at least one node from among the nodes from a user, and
the control unit automatically obtains second ultrasound images based on the selected node(s).

8. The ultrasound diagnosis apparatus of claim 5, wherein the input unit receives an input for selecting at least one node from among the nodes from a user, and
the control unit controls to automatically obtain second ultrasound images based on nodes other than the selected node(s).

9. The ultrasound diagnosis apparatus of claim 5, wherein the input unit is further configured to receive an input related to a sequence of nodes regarding at least two from among the nodes from a user, and
the control unit is further configured to determine the viewpoint based on the received input related to the sequence of nodes.

10. The ultrasound diagnosis apparatus of claim 5, wherein the input unit receives an input related to a speed of moving a viewpoint between nodes from a user, and
the control unit controls to move the viewpoint based on the speed of moving a viewpoint and obtains the second ultrasound images.

11. The ultrasound diagnosis apparatus of claim 10, wherein the input related to a speed of moving a viewpoint comprises moving time between nodes.

12. The ultrasound diagnosis apparatus of claim 1, wherein the control unit extracts first information comprising the nodes and the trunk lines from the ultrasound image by performing an image processing including a centerline extracting algorithm.

13. The ultrasound diagnosis apparatus of claim 12, wherein the control unit moves a viewpoint based on the first information and automatically obtains the second ultrasound images.

14. The ultrasound diagnosis apparatus of claim 1, wherein the control unit controls to move a viewpoint along trunk lines between the nodes and obtains second ultrasound images.

15. The ultrasound diagnosis apparatus of claim 1, wherein the control unit controls to display at least one of the nodes and the trunk lines passed by a viewpoint.

16. The ultrasound diagnosis apparatus of claim 15, wherein the control unit controls to display at least one from among the nodes and the trunk lines passed by a viewpoint in a transparency, a color, or a shape different from the nodes and the trunk lines not passed by the viewpoint.

17. The ultrasound diagnosis apparatus of claim 1, wherein the second ultrasound image comprise a virtual endoscopic image based on ultrasound data.

18. The ultrasound diagnosis apparatus of claim 1, wherein the second ultrasound images comprise at least one of 2D images and 3D images.

\* \* \* \* \*